(12) United States Patent
Aghajani et al.

(10) Patent No.: US 12,263,217 B2
(45) Date of Patent: Apr. 1, 2025

(54) NUCLEIC ACID STABILIZING SOLUTION FOR VACCINES, THERAPY, DIAGNOSTICS, STORAGE, AND TRANSPORT

(71) Applicant: Daykin Molecular Systems, LLC, Atlanta, GA (US)

(72) Inventors: Erik Avaniss Aghajani, Glendale, CA (US); John H. Phillips, Toronto (CA); Randal H. Rudderman, Atlanta, GA (US); Robert Louis Mullen, Columbia, SC (US)

(73) Assignee: Daykin Molecular Systems, LLC, Atlanta, GA (US)

( * ) Notice: Subject to any disclaimer, the term of this patent is extended or adjusted under 35 U.S.C. 154(b) by 406 days.

(21) Appl. No.: 17/541,325

(22) Filed: Dec. 3, 2021

(65) Prior Publication Data

US 2022/0193229 A1      Jun. 23, 2022

Related U.S. Application Data

(60) Provisional application No. 63/130,080, filed on Dec. 23, 2020.

(51) Int. Cl.
*A61K 39/39*      (2006.01)
*A61K 39/00*      (2006.01)

(52) U.S. Cl.
CPC .......... *A61K 39/39* (2013.01); *A61K 2039/54* (2013.01); *A61K 2039/55511* (2013.01)

(58) Field of Classification Search
CPC .................................................... A61K 39/39
See application file for complete search history.

(56) References Cited

U.S. PATENT DOCUMENTS 9,254,265 B2    2/2016   Geall et al.
10,022,435 B2   7/2018   Ciaramella et al.
(Continued)

OTHER PUBLICATIONS

Hongbo Liu, Yan Gan, Yanheng Wu, Hui Weng, Ping Lei, and Guanxin Shen. "Effects of different lysis buffers of nucleic acid purification kit on the stability of influenza virus RNA." Future Virology, vol. 9(6), 2014, pp. 549-555. (Year: 2014).*
(Continued)

*Primary Examiner* — Isaac Shomer
(74) *Attorney, Agent, or Firm* — TROUTMAN PEPPER LOCKE LLP; James E. Schutz; Mark Lehi Jones

(57) ABSTRACT

Chemical compositions and/or mixtures that allow nucleic acid to remain stable at ambient temperatures. The disclosed technology includes a solution and manufacturing methods thereof. The solution includes a chelating agent, a buffering agent, and a salt. The solution is configured to protect RNA and/or an RNA-based vaccine added to the solution and prevents or reduces degradation of the RNA and/or the RNA-based vaccine for a duration of 2 to 180 days over a temperature range of −20 degrees C. to +38 degrees C. The chelating agent can comprise ethylenediaminetetraacetic acid (EDTA). The buffering agent can comprise tris(hydroxymethyl)aminomethane (TRIS). The salt can comprise NaCl. The solution is configured to preserve an injectable mRNA vaccine added to the solution, and the solution is safe for injection into mammals.

17 Claims, 18 Drawing Sheets

(56) References Cited

U.S. PATENT DOCUMENTS

| | | | | |
|---|---|---|---|---|
| 2004/0038336 | A1* | 2/2004 | Baker | C07K 14/70546 435/325 |
| 2006/0024670 | A1* | 2/2006 | Luke | A61K 39/12 435/456 |
| 2009/0222941 | A1* | 9/2009 | Taguchi | C12Q 1/6895 435/6.12 |
| 2009/0304722 | A1* | 12/2009 | Theisen | A61P 31/04 435/7.1 |
| 2012/0186449 | A1* | 7/2012 | Yaghi | C07F 1/005 548/255 |
| 2013/0195969 | A1 | 8/2013 | Geall et al. | |
| 2014/0056942 | A1 | 2/2014 | Qiao et al. | |
| 2016/0310584 | A1 | 10/2016 | Frutsch et al. | |
| 2016/0326575 | A1 | 11/2016 | Mulbe et al. | |
| 2019/0351044 | A1 | 11/2019 | Jasny et al. | |

OTHER PUBLICATIONS

Anne-Lise Fabre, Marthe Colotte, Aurelie Luis, Sophie Tuffet, and Jacques Bonnet. "An efficient method for long-term room temperature storage of RNA." European Journal of Human Genetics, vol. 22, 2014, pp. 379-385. (Year: 2014).*
Katalin Karikó et al. "Incorporation of Pseudouridine Into mRNA Yields Superior Nonimmunogenic Vector With Increased Translational Capacity and Biological Stability." Molecular Therapy, vol. 16 No. 11, Nov. 2008, pp. 1833-1840. (Year: 2008).*
Germano Cecere and Alla Grishok. "RNA Chromatin Immunoprecipitation (RNA-ChIP) in Caenorhabditis elegans." Bio-protocol LLC, vol. 4, Issue 24, Dec. 20, 2014, http://www.bio-protocol.org/e1358 pp. 1-9. (Year: 2014).*
US Department of Health and Human Services. COVID-19 Vaccines. https://www.hhs.gov/coronavirus/covid-19-vaccines/index.html accessed Aug. 16, 2024, 12 printed pages. (Year: 2024).*
Linde Schoenmaker et al. "mRNA-lipid nanoparticle COVID-19 vaccines: Structure and stability." International Journal of Pharmaceutics, 601 (2021) 120586, pp. 1-13. (Year: 2021).*
Earle Stellwagen and Nancy C. Stellwagen. "The free solution mobility of DNA in Tris-acetate-EDTA buffers of different concentrations, with and without added NaCl." Electrophoresis, vol. 23, 2002, pp. 1935-1941. (Year: 2002).*
A simple salting out procedure for extracting DNA from human nucleated cells. S.A.M Wer, D.D.Dykes and H.F. Polesky. Memorial Blood Center of Minneapolis, 23(M Park Avenue South, Minneapolis, MN 55404, USA. Nucleic Acids Research. vol. 16 No. 3 1988. IR L Press Limited, Oxford, England.
A thermostable messenger RNA based vaccine against rabies. Lothar Stitz, Annette Vogel, Margit Schnee, Daniel Voss, Susanne Rauch,Thorsten Mutzke, Thomas Ketterer, Thomas Kramps, Benjamin Petsch. PLOS Neglected Tropical Diseases | https://doi.org/10.1371/journal.pntd.0006108 Dec. 7, 2017.
An Update on mRNA-Based Viral Vaccines. Subbiah Jeeva, Ki-Hye Kim, Chong Hyun Shin, Bao-Zhong Wang and Sang-Moo Kang. Vaccines 2021, 9, 965 . . . https://doi.org/10.3390/vaccines9090965.
A Thermostable mRNA Vaccine against COVID-19. Na-Na Zhang, Xiao-Feng Li, Yong-Qiang Deng, You-Chun Wang, Bo Ying, Cheng-Feng Qin. 2020, Cell 182, 1271-1283. Sep. 3, 2020 ª 2020 Elsevier Inc. https://doi.org/10.1016/j.cell.2020.07.024.
Chemical profiling of DNA G-quadruplex-interacting proteins in live cells. Xiaoyun Zhang 1,5, Jochen Spiegel 2,5, Sergio Martinez Cuesta 1,2,4, Santosh Adhikari 1 and Shankar Balasubramanian. Nature Chemistry | vol. 13 | Jul. 2021 | 626-633 | www.nature.com/naturechemistry.
Designing a novel mRNA vaccine against SARS-CoV-2: An immunoinformatics approach. Ishtiaque Ahammad, Samia Sultana Lira. International Journal of Biological Macromolecules 162 (2020) 820-837.
Developing mRNA-vaccine technologies.Thomas Schlake, Andreas Thess, Mariola Fotin-Mleczek and Karl-Josef Kallen.RNA Biology 9:11, 1319-1330; Nov. 2012; © 2012 Landes Bioscience.
Development of miRNA-based therapeutic approaches for cancer patients. Ryou-u Takahashi, Marta Prieto-Vila, Isaku Kohama, Takahiro Ochiya. Cancer Science. 2019;110:1140-1147.
High throughput RNA sequencing utility for diagnosis and prognosis in colon diseases. Mamie Gao, Allen Zhong, Neil Patel, Chiraag Alur, Dinesh Vyas. World J Gastroenterol Apr. 28, 2017; 23(16): 2819-2825.
Lipid Nanoparticles Enabling Gene Therapies: From Concepts to Clinical Utility. Jayesh A. Kulkarni, Pieter R. Cullis, and Roy van der Meel. Nucleic Acid Therapeutics vol. 28, No. 3, 2018. DOI: 10.1089/nat.2018.0721.
MRNA-lipid nanoparticle COVID-19 vaccines: Structure and stability. Linde Schoenmaker , Dominik Witzigmann , Jayesh A. Kulkarni , Rein Verbeke, Gideon Kersten, Wim Jiskoot , Daan J.A. Crommelin f. International Journal of Pharmaceutics 601 (2021) 120586.
MRNA Vaccine Era—Mechanisms, Drug Platform and Clinical Prospection. Shuqin Xu, Kunpeng Yang, Rose Li and Lu Zhang. Int. J. Mol. Sci. 2020, 21, 6582; doi:10.3390/ijms21186582.
MRNA vaccine: a potential therapeutic strategy. Yang Wang , Ziqi Zhang , Jingwen Luo, Xuejiao Han , Yuquan Wei and Xiawei Wei. Wang et al. Molecular Cancer (2021) 20:33 . https://doi.org/10.1186/s12943-021-01311-z.
Nucleic acid protocols: Extraction and optimization. Saeed El-Ashrama, Ibrahim Al Nasre,f, Xun Suo. Biotechnology Reports 12 (2016) 33-39.
Opportunities and Challenges in the Delivery of mRNA-Based Vaccines. Abishek Wadhwa , Anas Aljabbari , Abhijeet Lokras , Camilla Foged and Aneesh Thakur. Pharmaceutics 2020, 12, 102; doi:10.3390/pharmaceutics12020102.
RNA Sequencing: Platform Selection, Experimental Design, and Data Interpretation. Yongjun Chu and David R. Corey. Nucleic Acid Therapeutics vol. 22, No. 4, 2012.
RNA therapeutics on the rise. Feng Wang, Travis Zuroske and Jonathan K. Watts. Nature Reviews | Drug Discovery vol. 19 | Jul. 2020 | 441.
RNA Therapy: Current Status and Future Potential. Young-Kook Kim. Chonnam Med J 2020;56:87-93. https://doi.org/10.4068/cmj.2020.56.2.87.
RNA-based pharmacotherapy for tumors: From bench to clinic and back. Xiangping Lianga, Dongpei Lib, Shuilong Lengc, Xiao Zhua. Biomedicine & Pharmacotherapy 125 (2020) 109997.
Simple Methods and Rational Design for Enhancing Aptamer Sensitivity and Specificity. Priya Kalra, Abhijeet Dhiman, William C. Cho, John G. Bruno and Tarun K. Sharma. Frontiers in Molecular Biosciences www.frontiersin.org. May 2018 | vol. 5 | Article 41.
Room Temperature. Biological Sample Storage. Stanford University Pilot. Gregory D. Jensen, Management Consultant, Sustainable BioVentures. May 2009.
The Effect of N/P Ratio on the In Vitro and In Vivo Interaction Properties of PEGylated Poly(2-(dimethylamino)ethyl methacrylate)-Based siRNA Complexes. Dana J. Garya, Jung Bin Minb, Youngwook Kimb, Keunchil Parkb, and You-Yeon Wona. Macromol Biosci. Aug. 2013 ; 13(8): 1059-1071. doi:10.1002/mabi.201300046.
The Limitless Future of RNA Therapeutics. Tulsi Ram Damase, Roman Sukhovershin, Christian Boada, Francesca Taraballi. Roderic I. Pettigrew, and John P. Cooke. Frontiers in Bioengineering and Biotechnology. Mar. 2021 | vol. 9 | Article 628137.
The Many Pathways of RNA Degradation. Jonathan Houseley and David Tollervey. Cell 136, 763-776, Feb. 20, 2009.
The nano delivery systems and applications of mRNA Mingyuan Li, Yuan Li, Shiqin Li, Lin Jia, Haomeng Wang, Meng Li, Jie Deng, Ali Zhu , Liqiao Ma, Weihong Li , Peng Yu , Tao Zhu. European Journal of Medicinal Chemistry 227 (2022) 113910.
The promise of mRNA vaccines: a biotech and industrial perspective. Nicholas A. C. Jackson1, Kent E. Kester , Danilo Casimiro, Sanjay Gurunathan, and Frank DeRosa. www.nature.com/npjvaccines. npj Vaccines (2020) 11.
Treatment and prevention of lipoprotein(a)-mediated cardiovascular disease: the emerging potential of RNA interference therapeutics. Daniel I. Swerdlow , David A. Rider, Arash Yavari , Marie Wikström Lindholm , Giles V. Campion, and Steven E. Nissen. Cardiovascular Research (2021) 00, 1-14 Review.

(56) References Cited

OTHER PUBLICATIONS

RNA Vaccines against Infectious Diseases: Vital Progress with Room for Improvement Hana M. Abdelzaher , Asmaa S. Gabr , Basma M. Saleh , Rana M. Abdel Gawad, Ahmed A. Nour , and Anwar Abdelanser. Vaccines 2021, 9, 1211. https://doi.org/10.3390/vaccines9111211.

Lipid Nanoparticles From Liposomes to mRNA Vaccine Delivery, a Landscape of Research Diversity and Advancement. Rumiana Tenchov, Robert Bird, Allison E. Curtze, and Qiongqiong Zhou. ACS Nano 2021, 15, 16982-17015.American Chemical Society.

Recent developments of magnetic beads for use in nucleic acid purification. Peter R. Levisona ,*, Stephen E. Badgera, Jon Dennisa, Prit Hathib, Martin J. Daviesb, p c Ian J. Bruce , Dieter Schimkat. Journal of Chromatography A, 816 (1998) 107-111.

Isolation of the Nucleic Acid of Newcastle Disease Virus (NDV)* by Peter H. Duesberg and William S. Robinson. vol. 54, 1965 Biochemistry: Duesberg and Robinson. 794-800.

Enzymatic synthesis of biotin-labeled polynucleotides: Novel nucleic acid affinity probes. Pennina R. Langer, Alex A. Waldrop, and David C. Ward. Proc. Natl Acad. Sci. USA . vol. 78, No. 11, pp. 6633-6637, Nov. 1981. Biochemistry.

The Human Immunodeficiency Virus Type 1 Gag Polyprotein Has Nucleic Acid Chaperone Activity: Possible Role in Dimerization of Genomic RNA and Placement of tRNA on the Primer Binding Site. Ya-Xiong Feng,1 Stephen Campbell,1 Demetria Harvin, Bernard Ehresmann, Chantal Ehresmann,and Alan Rein. Journal of Virology, May 1999, p. 4251-4256 vol. 73, No. 5.

Kinetics and mechanism of polyamide ("peptide") nucleic acid binding to duplex DNA. Vadim V. Demidovtt§, Michael V. Yavnilovich, Boris P. Belotserkovskih, MAxIM D. Frank-Kamenetski, and Peter E. Nielsen, Proc. Natl. Acad. Sci. USA. vol. 92, pp. 2637-2641, Mar. 1995. Biochemistry.

Evidence for Nucleic Acid Binding Ability and Nucleosome Association of Bombyx mori Nucleopolyhedrovirus BRO Proteins. Evgueni A. Zemskov, Wonkyung Kang, and Susumu Maeda. Journal of Virology, Aug. 2000, p. 6784-6789. vol. 74, No. 15.

Higher order DNA structure in macronuclear chromatin of the hypotrichous ciliate Oxytricha nova. Hans J. Lipps*t, Wilhelm Gruissem, and David M. Prescott. Proc. Natl Acad. Sci. USA. vol. 79, pp. 2495-2499, Apr. 1982 Biochemistry.

3D printed integrated separator with hybrid micro-structures for high throughput and magnetic-free nucleic acid separation from organism samples. Peipei Li a,b, Menghang Li b,c, Zhijie Yuan c, Xiaobin Jiang c,*, Dongmei Yue b, Bo Ye b, Zhenjun Zhao b, Jingwei Jiang b, Qi Fan b, Zunchun Zhou b, Haixia Chen a. Separation and Purification Technology 271 (2021).

High throughput quantification of short nucleic acid samples by capillary electrophoresis with automated data processing. Tyler L. Dangerfield, Nathan Z., Huang, Kenneth A.Johnson. Analytical Biochemistry vol. 629, Sep. 15, 2021.

Synthesis and validation of DOPY: A new gemini dioleylbispyridinium based amphiphile for nucleic acid transfection Eva Aubets, Rosa Griera, Alex J.Felixad, Gemma Rigola, Chiara Sikorskia, David Limónbd, Chiara Mastrorosaa, Maria Antònia Busquet, Lluïsa Pérez-García, Véronique Noéad, Carlos J.Ciudadad. European Journal of Pharmaceutics and Biopharmaceutics, vol. 165, Aug. 2021, pp. 279-292.

Molecular Assessment of Genetic Diversity Among Male, Female and Hermaphrodite Simarouba speciesUsing Random Amplified Polymorphic Deoxyribose Nucleic Acid Markers.Vaidya Gayatri, Naik. International Journal of Current Research and Review Original Research . vol 13 • Issue 11 • Jun. 2021.

Electrochemical biosensing of DENV nucleic acid amplified with triplet nanostructure-mediated dendritic hybridization chain reaction. Jinling Fua, Jie Wub, Rui Zhanga, Qiang Wua, Huangxian Jub Sensors and Actuators B: Chemical vol. 345, Oct. 15, 2021, 130436.

High-efficient nucleic acid separation from animal tissue samples via surface modified magnetic nanoparticles. Separation and Purification Technology. Peipei Liab, Menghang Lib, Fan Zhang, Mengyuan Wuc, Xiaobin Jiang, BoYeb, Zhenjun Zhaob, Dongmei Yue,Qi Fan, Haixia Chen vol. 262, May 1, 2021.

Fuel strand-powered self-propelled electrochemical DNA machine for enzyme-free and distinctly amplified detection of nucleic acid with tunable performance. Zhen Zhao, Zhiqiang Chen, Dengren Liu, Li Wang. Biosensors and Bioelectronics vol. 171, Jan. 1, 2021.

Prominent increases of nuclear DNAJA3 and cytosolic STAT1 with nucleic acid sensors underlie innate immunity activation in ClpP-null mouse. Antonia Maletzko, Jana Key, Ilka Wittig, Suzana Gispert, Gabriele Koepf, Júlia Canet Pons, Sylvia Torres-Odio, A. Phillip West, Georg Auburger. Preprints.org > life sciences > biochemistry > doi: 10.20944/preprints202105.0021.v1. Approved: May 4, 2021 / Online: May 4, 2021 (14:08:18 CEST).

Chemical profiling of DNA G-quadruplex-interacting proteins in live cells. Xiaoyun Zhang, Jochen Spiegel, Sergio Martinez Cuesta, Santosh Adhikari, and Shankar Balasubramanian. Nature Chemistry | vol. 13 | Jul. 2021 | 626-633.

A mini DNA-RNA hybrid origami nanobrick. Lifeng Zhou, *a Arun Richard Chandrasekaran, a Mengwen Yan, b Vibhav A. Valsangkar, ab Jeremy I. Feldblyum, b Jia Sheng ab and Ken Halvorsen. Nanoscale Adv., 2021, 3, 4048-4051.

Quantitative real-time PCR with high-throughput automatable DNA preparation for molecular screening of Nosema spp. in Antheraea pernyi. Peipei Li, Rui Mi, Rui Zhao, Xiangcun Li,Bo Zhang, Dongmei Yue, Bo Ye, Zhenjun Zhao, Linmei Wang,Youmin Zhu, Chen Bao, QiFanbXiaobinJiangcYaozhouZhanga Journal of Invertebrate Pathology vol. 164, Jun. 2019, pp. 16-22.

Genome-wide detection and quantitation of RNAdistribution by ChIRC13a-seq. Fan Yang, Bogdan Tanasa, Rudi Micheletti,Kenneth A. Ohgi, Aneel K. Aggarwal, Michael G. Rosenfeld. https://protocolexchange.researchsquare.com/article/pex-1416/v1. Jul. 1, 2021.

Directed evolution of orthogonal RNA-RBP pairs through library-vs-library in vitro selection. Keisuke Fukunaga and Yohei Yokobayashi *. Nucleic Acids Research, 2021 1 https://doi.org/10.1093/nar/gkab527.

Simultaneous Recovery of RNA and DNA from Soils and Sediments. Richard A. Hurt,1 Xiaoyun Qiu,1 Liyou Wu,1,2 Yul Roh,1 A. V. Palumbo,1 J. M. Tiedje,2 and Jizhong Zhou1. Applied and Environmental Microbiology, 0099-2240/01/$04.000 DOI: 10.1128/AEM.67.10.4495-4503.2001. Oct. 2001, p. 4495-4503.

Decellularization for the retention of tissue niches, Moffet et al,. Journal of Tissue Engineering, vol. 13, pp. 1-29, 2022.

CDC Moderna COVID-19 Vaccine, Vaccine Preparation and Administration Summary.

CDC Pfizer-BioNTech COVID-19 Vaccine, Storage and Handling Summary.

European Search Report dated Oct. 18, 2024, EP application 21911865. 0-1109 / 4267181 PCT/US2021061696.

* cited by examiner

```
                                              ┌─ 1400
                                              ▼
┌─────────────────────────────────────────────────────────┐
│ Preparing a solution, the solution comprising: a chelating agent      │ 1402
│ comprising ethylenediaminetetraacetic acid (EDTA); a buffering agent  │
│ comprising tris(hydroxymethyl)aminomethane (TRIS); and a salt         │
│ comprising NaCl                                                       │
└─────────────────────────────────────────────────────────┘
                              │
                              ▼
┌─────────────────────────────────────────────────────────┐
│ Configuring concentrations of the chelating agent, buffering agent, and│ 1404
│ salt for final molarities prior to addition of a vaccine to the solution│
└─────────────────────────────────────────────────────────┘
                              │
                              ▼
┌─────────────────────────────────────────────────────────┐
│ Configuring a final molarity of the chelating agent to be in the range of│ 1406
│ 0.026m to 1.0m and configuring a final molarity of the salt to be in the │
│ range of 0.15m to 3.0m                                                   │
└─────────────────────────────────────────────────────────┘
                              │
                              ▼
┌─────────────────────────────────────────────────────────┐
│ Configuring the solution so that it is safe for injection into mammals and│ 1408
│ so that it protects vaccine added to the solution and prevents degradation│
│ of the vaccine for a duration of 1 to 180 days over a temperature range of│
│ minus 20 degrees C to + 38 degrees C.                                    │
└─────────────────────────────────────────────────────────┘
```

FIG. 14

NUCLEIC ACID STABILIZING SOLUTION FOR VACCINES, THERAPY, DIAGNOSTICS, STORAGE, AND TRANSPORT

CROSS-REFERENCE TO RELATED APPLICATIONS

This application claims priority to U.S. Provisional Patent Application Ser. No. 63/130,080, entitled "RNA Stabilizing and Storage Solution," filed 23 Dec. 2020, the contents of which are incorporated herein by reference as if presented in full.

FIELD

This disclosure is related to nucleic acid stabilization, and in particular, to reducing degradation of RNA for storage and transportation at ambient and elevated temperatures and for use in diagnostics and therapeutics including vaccines.

BACKGROUND

Ribonucleic acid (RNA) is an essential nucleic acid component in health and medical treatments, including but not limited to pharmacologic modification of disease states. RNA species are also used in the diagnostic and therapeutic treatment of both normal and pathology scenarios, including genetic diseases, exogenous diseases, including infectious diseases (bacterial, viral, and other) and illnesses and their treatments. Genetic translation to the multiple species including tRNA (transfer RNA), mRNA (messenger RNA), and rRNA (Ribosomal RNA), RNAi (RNA Interference), siRNA (small interfering RNA) is used to study and guide treatment modalities of disease states.

mRNA vaccines have several benefits over other types of vaccines. A general advantage of mRNA vaccines is that their development is relatively fast. Flexible design, standardized production processes and relatively short-lived cytoplasmic presence make mRNA vaccines very powerful, especially in a pandemic situation with rapidly mutating viruses.

The conventional view of RNA casts it in a supporting role as the intermediary between DNA and protein, and a passive conduit for information, which is how the most familiar form of messenger RNA works. But only a small fraction of RNA molecules in cells are mRNAs.

Not only does RNA carry instructions for making proteins, but RNAs can also help to turn genes on and off, aid chemical reactions, modify other RNAs, and build proteins by transporting amino acids and linking them together. In turn, these diverse roles have inspired a host of ideas about how to harness RNA for use in medicine.

mRNA (messenger RNA) transfers genetic information from DNA to facilitate protein formation. Due to the positive charge of RNA, its size, and fragility, and ease of degradation at multiple temperatures, innovative methods have been developed to deliver the RNA into cells.

mRNA is typically stored at low temperatures to facilitate structural and functional stability short-term and long-term, which can be a significant expense. mRNA vaccines present additional challenges due to constructs necessary to allow for predictable functional ability, including methods used to assist in delivery.

It is essential to stabilize intact functional nucleic acids including DNA and RNA species (for vaccines, therapeutics, diagnostics, etc.) in a manner that prevents degradation during manufacturing, storage, transport, and application. To minimize degradation of nucleic acid in biological samples, it is standard practice to maintain constructs with nucleic acids (RNA and DNA) at −80 C and kept frozen in storage (−80° C. to −20° C.). The costs, logistics and infrastructure needed to ensure products are maintained at low temperatures during manufacturing, transport to medical facilities, and stored under optimal conditions prior to use, pose significant challenges and risks, especially in large-scale and population-based treatment applications. It is highly desirable to utilize a reliable method for delivery of stable verifiably intact nucleic acid components while reducing reliance on refrigeration.

The utilization of RNA is of particular interest and importance in the development of vaccines that utilize RNA segments for targeted therapy. However, one of the issues with RNA is that it is susceptible to damage, cleavage, and degradation both during extraction and in storage, manufacturing, and application. RNA is chemically significantly more reactive than DNA due in part to hydroxyl groups in both the 2' and 3' positions. Multiple mechanisms of degradation exist and must be addressed for predictable RNA management, including oxidation by multiple reactive oxygen species, exposure to metallic ions, multiple catalytic agents, enzymatic and nuclease species, and high temperatures. Molecules exist in biological systems to degrade RNA (RNase), and contamination from a variety of RNase (ribonucleases) species will rapidly degrade RNA. RNase and some ribosomes also act to cleave the phosphodiester linkage via transesterification. There are a variety of mechanisms that result in mRNA degradation. Chemical degradation encompasses the modifications of bonds in the mRNA molecule. Physical instability includes denaturation (loss of secondary and tertiary structure), which also comprises processes such as aggregation and precipitation, which negatively affect mRNA translation. Chemical degradation of mRNA in vitro mainly occurs through hydrolysis and oxidation. Hydrolysis predominantly occurs via the phosphodiester bonds that form the backbone of the mRNA molecule. The transesterification reaction leading to an mRNA strand break starts with a nucleophilic attack by the 2'OH group on the ribose on the phosphate ester bond leading to a break at the P—O5' ester bond. This process requires water and can be catalyzed by nucleases, but also by the mRNA molecule itself and other exogenous factors (such as Brønsted acids and bases). Oxidation, in contrast, affects the nucleobases and to a lesser extent the sugar groups of the mRNA's ribose units. Oxidation can lead to the cleavage of bases, strand breakage and the alteration of the secondary structure of the mRNA.

RNases may not require metal ions due to the hydroxyl group reactivity. Diester bonds linking phosphate and ribose residues may be hydrolyzed disrupting RNA. Degradation is commonly the result of spontaneous cleavage of the phosphodiester linkage through transesterification resulting from a nucleophilic effect of the phosphorus atom by the neighboring 2'OH. H2O also provides hydroxyl or hydronium ions allowing proton transfer.

Water assists in the degradation process by facilitating proton transfer. Most systems and techniques used to stabilize RNA use dehydration to inhibit degradation. RNA is most commonly stored at −20 to −80 degrees C. and even at these temperatures has been known to degrade due in part to residual ribonucleases remaining active. RNA is notorious for degradation as well due to extensive opportunities for environmental contamination. The variability in degradation, therefore, requires costly methods and typically large sample sizes to ensure adequate intact specimens for study and treatment algorithms.

Conventional RNA stabilizing and/or storage systems available typically involve extraction and then processing for storage. Solutions involve buffering and or chelating agents to inactivate organic compounds that degrade the RNA, or desiccation, or storage in absence of air. The solutions available to store samples are often toxic to skin and soft tissue, cannot be ingested, are not compatible with injection into humans and animals, and may require additional handling and processing prior to downstream testing. Some applications require storage in a fully dried state or immediate placement in cold storage upon rehydration or addition of liquids. Conventional processes may also include combinations of the above.

Multiple methods of RNA storage have been described, including dehydration with additives, storage with reducing agents, multiple-step procedures for desiccation, purification, and protection from oxygen and water by placement in airtight containers.

Vaccines

The mRNA vaccines that are used to protect against SARS-CoV-2 (the virus that causes COVID-19) are the first of their kind to be licensed for widespread human use.

Studies and clinical trials on RNA vaccines for other viruses—including cancers—have been going on for a decade. These types of vaccines introduce a specific RNA sequence into the body, which causes the body's ribosomes to temporarily express a specific, harmless viral protein (after which the foreign RNA molecules are degraded). In turn, this impacts the immune system to respond in such a way that produces strong protection against this virus the next time it encounters it.

This is unlike conventional vaccines, which require either a harmless, inactive form of a virus or small proteins or protein fragments made by a virus, to train the immune system. Designing and synthesizing an RNA sequence that provides the body with instructions is also easily and quickly done.

One of the biggest hurdles in making effective RNA-based drugs has been the relative instability of the molecules. These degrade rapidly when exposed to certain common enzymes and chemicals, so need to be kept at very low temperatures—in some cases below −70° C.

There exist many challenges and opportunities in the developing mRNA-based vaccines, as discussed in the following journal papers: (1) Developing mRNA-vaccine technologies, Schlake et. al., RNA Biology 9:11, 1319-1330; November 2012; © 2012 Landes Bioscience; (2) mRNA Vaccine Era-Mechanisms, Drug Platform and Clinical Prospection, Xu et. al., Int. J. Mol. Sci. 2020, 21, 6582; doi:10.3390/ijms21186582; (3) Designing a novel mRNA vaccine against SARS-CoV-2: An immunoinformatics approach, I. Ahammad, S. S. Lira, International Journal of Biological Macromolecules 162 (2020) 820-837; and (4) Opportunities and Challenges in the Delivery of mRNA-Based Vaccines, Wadhwa, et. al., Pharmaceutics 2020, 12, 102; doi:10.3390 pharmaceutics 12020102; and (5) The significance of acid/base properties in drug discovery, Manallack et al., Chem Soc Rev, 2013; 42(2):485-496. doi:10.1039/c2cs35348b; the contents of which are incorporated herein as if presented in full.

The first obstacle for mRNA vaccines is that naked mRNA is quickly degraded upon injection by ribonucleases (RNase), which are abundant in the extracellular environment. Research on mRNA vaccines has demonstrated that naked mRNA is quickly degraded after administration.

Prior storage and transport systems and solutions do not allow for long-term verifiable storage in systems that can easily be transported, stored, and delivered to the end-user for applications such as the transport of vaccines. Additional common risk factors for vaccine degradation are aluminum salt aggregation due to freezing and inactivation of the attenuated virus by exposure to elevated temperature, due to additional factors often unknown in traditional vaccine management. Additional systems have been proposed and developed including nanoparticles, polymers such as polyethylene glycol, and sucrose, and lypholysed glass to create capsomeres to maintain critical conformational epitopes. There are several commercial products for preservation during sample collection: RNAlater Tissue Collection: RNA Stabilization Solution (Life Technologies, Carlsbad, Calif.), RNAlater RNA Stabilization Reagent (Qiagen, Valencia, Ca), PAXgene tubes (PreAnalytix, Valencia, Calif.), RNAstable (Biomatrica, San Diego, Calif.), RNAshell (Imagene), Gentegra (integenX), Ambion, (ThermoFisher), Isohelix BuccalFix (Bocca Scientific), RNA Protect, and RNA Shield (Cambridge Bioscience). Alternatively, RNA can be protected within a physical barrier employing materials similar to those used in DNA encapsulation: liposomes, micelles, or polymers.

Storage, stabilization, and transport of RNA, including mRNA, remains problematic and is often done at reduced temperatures. Even at transport at 2-8 degree C., 80% or more of the cost is related to the cold chain issue. In addition, vaccine degradation facilitated by water includes oxidation, deamidation, hydrolysis, peptide fragmentation, disulfide exchange, dimerization, aggregation, and structural modification resulting in incorrect and or altered antigen activity. These challenges, including the risk of degradation, can add significant costs in handling, storage, transport, and delivery of mRNA therapeutics including vaccines.

In order to effectively distribute a vaccine worldwide, it should have a sufficiently long shelf life, preferably at ambient temperatures, and be stable in shipping where higher temperatures may occur. Even areas where refrigerator temperatures (2-8° C.) may be available, the requirement of storing the mRNA-LNPs at a low temperature, and particularly the very low temperature of −60 to −90° C. for some long-term storage is a major obstacle to vaccine distribution, transport, and storage among end-users worldwide.

Naked mRNA is ineffective in entering the cells, unstable, and easily destroyed. Nucleic acids by their hydrophilic nature and negative charge are impeded by passive diffusion across plasma membranes. Multiple factors including uptake by phagocytosis and degradation by endogenous nucleases interferes with their delivery and efficacy. Nucleic acids therefore often require constructs for protection from degradation and for efficient and targeted delivery. The development of lipid nanoparticles (LNP) to facilitate the delivery of RNA molecules into the cells in vivo has become a major step in innovating RNA technologies.

Currently, the commonly used nano delivery systems include lipid nano particles which are used to transfer RNA genetic material into a cell to induce protein expression. Lipid nano particles (LNPs) include liposomes, lipid polycomplexes, polymer materials, micelles, polypeptides, protamine, electroporation, and an extensive variety of compounds that are highly efficient, nontoxic, tissue, organ, or cell-selective LNP formulations. More recent lipid nanoparticles have been designed to optimize targeted delivery and efficiency, an include solid lipid nanoparticles, nanostructured lipid carriers, and cationic lipid—nucleic acid complexes. LNPs and liposome formulations may be used for the storage and transport of RNA or other nucleic acids species. Polymer based delivery systems have been developed for mRNA delivery such as Polyethylenimine (PEI), graphene oxide (GO)-polyethylenimine (PEI) complexes, a variety of tailored polyplex nanomicelles, and cationic peptides including cationic cell-penetrating peptides (CPPs) and anionic peptides. The components of LNP typically include an amine-group ionizable lipid, cholesterol, PEGylated lipid, and a helper lipid such as distearoyl-phosphatidylcholine (DSPC).

The LNPs in mRNA COVID-19 vaccines consist of four main components: a neutral phospholipid, cholesterol, a polyethylene-glycol (PEG)-lipid, and an ionizable cationic lipid. The latter contains positively charged ionizable amine groups (at low pH) to interact with the anionic mRNA during particle formation and also facilitate membrane fusion during internalization. In addition, PEG-lipid is used to control the particle size and act as a steric barrier to prevent aggregation during storage.

A key aspect of LNPs and the characteristic that makes them different from liposomes (spherical vesicles with at least one lipid bilayer and an aqueous core) is the presence of lipids in the core, although data from several studies indicate that water is also present to some extent. This would mean that the mRNA could be exposed to an aqueous environment, even when it is encapsulated.

A special feature of mRNA is that even one change (strand break, or oxidation of the bases) in the long mRNA strand (typically between 1000 and 5000 nucleotides long) can stop translation. This makes mRNA vaccines quite different from other vaccines in which small changes of the antigens do not necessarily have a measurable effect on their efficacy. Consequently, for mRNA vaccines, it is critical to monitor the integrity of the full molecule.

The stability of both the mRNA component and constructs for effective delivery to the target are critical for local and global distribution. Besides mRNA integrity, the stability of LNPs is critical for the quality of mRNA-LNP vaccines. LNPs can undergo chemical and physical instability. Chemical instability comprises the degradation of the lipids in the LNPs that are susceptible to hydrolysis and oxidation. Lipid oxidation can occur in unsaturated fatty acid moieties and with cholesterol, potentially as a result of a hydroperoxide attack, an impurity present in the PEG-group of PEG2000-C-DMG. Oxidative impurities may also result in the oxidation of encapsulated mRNA. The carboxylic ester bonds in lipids, such as DSPC and the ionizable cationic lipids, are susceptible to temperature- and pH-dependent hydrolysis.

Another key aspect of LNP stability is physical degradation. There are three main types of physical instability that can occur: aggregation, fusion, and leakage of the encapsulated pharmaceutical ingredient. Aggregation of LNPs during storage and fusion of LNPs has been reported. To increase stability on the shelf, LNPs are often formulated with PEG-lipids. The PEG molecules at the surface prevent the individual LNPs from aggregating.

At refrigerator temperatures, 2-8° C., the Pfizer/BioNTech and Moderna vaccines are stable for 5 and 30 days, respectively. Both companies provide detailed handling instructions for the end-user. Such temperature requirements severely impact the logistics of the storage, transport, and distribution of these vaccines.

Hypersensitivity reactions that are rarely observed upon intramuscular injection of the mRNA-LNP COVID-19 vaccines may be related to the PEG-lipids. Stabilized lipid-based systems such as polysarcosine-modified lipids have been introduced to limit aggregation while reducing the immunostimulatory response. Alternative lipids to prevent aggregate formation have been investigated and may be used in the preparation or delivery of RNA vaccines.

Reported "shelf lives" of current mRNA vaccines vary widely from days to months over temperatures ranging from about −80° C. to about +8° C. Thus, creating more stable mRNA-LNP vaccines will require stabilizing the mRNA at a wider temperature range as well as stabilizing the lipid constructs and vehicles used to deliver vaccines a wider temperature range.

The base sequence and secondary structure of mRNA influence the rate of hydrolysis, further leading to degradation. Specifically, base-stacking may decrease the cleavage rate of phosphodiester bonds. A difference between the CureVac, Pfizer/BioNTech and Moderna vaccines is that the latter two have single nucleoside incorporations of I-methyl-pseudouridine. A previous study has shown that this modification improves RNA secondary structure stability. CureVac uses GC-enrichment, with a potentially similar effect. Limiting hydrolysis which is a significant factor driving mRNA degradation is another component favorable in a stabilizing solution or method for RNA.

Multiple excipients in the formulations for mRNA vaccines serve as buffers, osmolytes and cryoprotectant, or have a dual or multiple effects. Moderna, for example, uses a Tris-HCl buffer that would have an additional stabilizing effect on nucleic acid macromolecules as it is also a hydroxyl radical scavenger.

The choice of the buffering system and osmolyte is important as the pH may change upon freezing, as has been shown for sodium phosphate buffered systems, in which a 3.5 pH-unit drop occurs upon freezing. Histidine buffers are more 'pH-resistant' upon freezing. But still, the pH may drop 0.5 units when cooling from 0° C. to ~-30° C. NaCl (osmolyte) solutions have a eutectic temperature of ~-21° C. Other excipients that could be added are antioxidants, non-reducing free radical scavengers (e.g., ethanol) or metal chelators. Optimization of pH is also important for mRNA vaccine stability, as the pH influences the hydrolysis rate of mRNA and also LNP stability. Generally, mRNA is most stable in a weakly basic environment. The pH of the Moderna and Pfizer/BioNTech vaccines is between 7 and 8. Apparent pH at the surface of the cationic, fully charged lipids could be higher than in the immediate surrounding aqueous medium. Future mRNA vaccines may require an additional modification of delivery and storage methods to maintain functionality, particularly at ambient temperatures globally.

As the presence of water initiates degradation reactions in mRNA-LNPs, lyophilization would be a logical step to improve the long-term stability of mRNA-LNP formulations. Studies with either mRNA or with LNPs suggest that lyophilization could be a possible way to increase the stability of the combination, mRNA-LNP, and could thereby allow for storage at higher temperatures than those currently required. However, lyophilization does have its downsides, as it requires reconstitution before administration and is a relatively expensive, energy- and time-consuming process. On the other hand, keeping the mRNA vaccines (deep) frozen, or at low temperatures during storage, transportation, at the delivery location, and for shelf life also comes at a significant cost.

An extensive variety of mRNA applications for personalized use can include vaccines (treatments) for protection of infectious diseases, vaccines (treatments) for genetic therapy for inherited or acquired diseases, vaccines (treatments) for tumors or cancers, vaccines (treatments) for metabolic/endocrine disorders, vaccines (treatments) for general aging and health preservation, optimization, or anticipated decline, vaccines (treatments) for intrauterine diseases, genetic or acquired, and general health vaccines (treatments) for concerns such as cardiac disease, neurogenic and physiologic decline, aging, and other applications.

mRNA application for delivery as vaccines for infectious diseases and where mRNA vaccine could activate both cellular and humoral immunity, achieving significant protection rate for viruses such as severe acute respiratory syndrome (SARS-CoV-2), influenza A virus, rabies virus, respiratory syncytial virus (RSV), Zika virus (Zika), human immunodeficiency virus (HIV1), Ebola virus (EBOV), and others have been developed or investigated. Active and passive immunity as well can be achieved against additional infectious agents.

Another function of an mRNA tumor vaccine is to prompt the cell mediated response, such as the typical T lymphocyte response, so as to achieve the aim of removing or reducing tumor cells without harming normal cells.

mRNA vaccines can be combined with other oncology therapies, such as checkpoint inhibitors and immune agonists, to achieve a more comprehensive oncology therapeutic effect.

A variety of vaccines targeting cancers are in development including Moderna mRNA-4157 Personalized tumor vaccines, mRNA-5671, mRNA-2416, mRNA-2752, and so on. Colorectal cancer, non-small cell lung cancer, pancreatic cancer, BioNTech BNT111 Advanced melanoma BNT112. Prostate cancer and high-risk localized prostate cancer BNT113 HPV16-positive solid cancers BNT114 Triple Negative Breast Cancer BNT115 Ovarian cancer BNT122 Melanoma, non-small cell lung cancer, bladder cancer, etc. CureVac AG e Non-small cell lung cancer.

There is a need for assays to enable general pharmaceutical tests, determine and monitor mRNA drug substance, determine and monitor mRNA-LNP drug product quality attributes and stability, characterize mRNA-encoded translation products, and/or characterize mRNA-lipid complexes.

There are also mRNA therapies, which produce functional proteins. Antisense oligonucleotides (ASCs), for example, are short stretches of modified DNA typically made up of about 13-25 nucleotides. These molecules prevent mRNA from being translated into protein by several mechanisms, including blocking the start of translation or tagging the mRNA for degradation. Inotersen is an ASO and is one of the amyloidosis drugs that are FDA approved.

ASOs can also alter splicing, the process that sculpts a precursor messenger RNA into its mature form. Two of these types of ASO received FDA approval in 2016: nusinersen, which targets a fatal inherited condition called spinal muscular atrophy; and eteplirsen, a treatment for Duchenne muscular dystrophy. The latter is an example of an 'exon' skipping drug, which uses an ASO to block only the mutated portion of a gene from being expressed. The result is a protein that is functional, but that lacks the mutated portion that causes pathology.

Because RNAi makes use of double-stranded molecules, these therapies are more challenging to get into cells than ASOs. However, fewer molecules are needed for the therapy to be effective. RNAi involves small interfering RNAs (siRNAs), 21-23 nucleotides long, or similar molecules such as microRNAs, to degrade mRNA and prevent it from being translated into protein. Another amyloidosis drug approved in 2018, patisiran, is an siRNA therapy.

RNA therapies that target proteins use a type of molecule known as an RNA aptamer. The molecule is designed to bind to a specific site on a specific protein to modulate its function. Pegaptanib, a treatment for a form of age-related macular degeneration in which blood vessels penetrate the retina and cause vision to deteriorate, is an example of such a drug. Pegaptanib binds to and blocks the function of the protein vascular endothelial growth factor, leading to a reduction in the growth and permeability of blood vessels in the eye. RNA aptamers might be useful in surgery and emergency medicine, in which their rapid action and reversibility could aid anesthesia and modulate blood clotting. Other RNA species including RNAi's and siRNAs may also be used in treatment therapies.

RNA therapies that use mRNAs are being used to develop personalized cancer vaccines, as well as vaccines for infectious diseases such as the Zika virus, which has been linked with the condition of microcephaly. Researchers are also exploring whether these types of treatments can be used as protein-replacement therapies for rare conditions such as the blood-clotting disorder hemophilia.

The biggest barrier to RNA therapy has long been delivering RNA to the correct place in the correct cells. The past several years have seen significant advances that have improved researchers' ability to get such drugs into liver cells which is an important development because so many proteins implicated in diseases are made in the liver.

The development of RNA therapeutics required that several major hurdles be overcome, specifically the (1) rapid degradation of exogenous RNA by RNases that are ubiquitous in the environment and tissues; (2) delivery of negatively charged RNA across hydrophobic cytoplasmic membrane; and (3) strong immunogenicity of exogenous RNA that caused cell toxicity and impaired translation into therapeutic proteins.

Drugs that target RNA can be identified, and in some instances customized, because researchers can sample RNA interactions and sequences linked to many different diseases from readily available databases. Drugs that target RNA have provided great promise in the treatment of very rare diseases, which previously lacked effective, existing treatments—such as Huntington's disease.

Drugs are also being designed which can target RNAs and modify or inhibit the function of certain genes or protein production—including those responsible for many diseases and symptoms. Several of these have now been used to successfully treat viruses, neurodegenerative diseases, and even in personalized medicine (treatments designed specifically for that patient).

RNA interference drugs are another area of research. These drugs silence a specific gene to treat a condition. Research into these types of drugs is currently underway for many conditions, including amyloidosis (a rare disease caused by a buildup of proteins in the body), acute hepatic porphyria (a rare metabolic disorder), and several cancers (including lung cancer).

More recently, certain groups of RNAs and proteins have been shown to change the sensitivity of diseases (particularly cancers) to treatment. This has made some cancers less resistant to conventional treatment as a result. This could potentially provide a valuable new combination therapy for hard-to-treat diseases.

An additional kind of RNA therapy focuses on replacing mRNA. Cystic fibrosis patients, for example, fail to make a functional protein called CFTR in their cell membranes. Scientists hope to have patients inhale particles containing healthy mRNA, replacing the dysfunctional CFTR protein in the lung. Translate Bio is an mRNA candidate to treat patients with cystic fibrosis, Moderna Therapeutics, is also developing a treatment for cystic fibrosis. Moderna is valued at over $7.5 billion-demonstrating the enthusiasm for these strategies.

Despite significant advances in treatment options, cardiovascular disease remains the number one cause of death in the world. mRNA vaccines may be used as a utility of RNA for targeting previously 'undruggable' pathways involved in the development and progression of cardiovascular disease by multiple pathways including epicardial injections which may provide evidence that direct injection of mRNA into an ischemic tissue may improve perfusion and function and other methods of delivery.

RNA technologies can be used to make personalized treatments. An example includes harvesting information from a human or animal sample, taking a pair of genetic profiles from the patient: one from a biopsy of the tumor, the other from a vial of healthy blood or other cells. Algorithms compare the nucleic acid sequences of the two samples and produce a list of targets, each encoding a different mutant protein expressed by the cancer cells that is predicted to be useful in training the immune system to attack the disease. RNA targeted therapy for the specific entity is then developed.

RNA is also being used to help develop new drugs. Most RNA therapies can be sorted into one of three broad categories: those that target nucleic acids (either DNA or RNA), those that target proteins, and those that encode proteins. Hybrid approaches that combine several RNA-based mechanisms into a single package are also emerging.

There are two main types of RNA therapy that target nucleic acids: (1) antisense oligonucleotides (ASOs); and (2) double-stranded molecules that operate through a cellular pathway known as RNA interference (RNAi) which degrades dysfunctional or harmful proteins in the cell.

RNA can also help other biomolecules find each other and help bring other proteins and RNAs together. These functions are crucial in managing the many levels of gene regulation, which is itself important for the proper functioning of the body.

RNA may be used for binding to molecules, antibiotics, dyes, specific proteins, fluorescent probes, molecules acting as protein or other based controllers, etc.

RNA may be used in applications for methods to detect known and novel (new) molecules including disease marking proteins, metabolic products in normal tissues, and diseased tissues.

RNA may be used in many other applications including self-cleaving ribosomes as engineered RNA controllers, riboswitches including those used with internal ribosome entry sites for activation or repression of gene expression, ribosome shunting, transacting non-coding RNA including molecules to regulate transcription or translation, applications that include aptamers or aptazymes fused to single guide RNAs, use with CRISPER technologies for control of gene expression, use with RNA controllers critical for ligand-induced regulation, and use for bacterial riposwitches to control transcription termination in response to specific molecules. These developments culminated in the 2018 approval, in both the United States and Europe, of two RNA-based therapies for hereditary ATTR amyloidosis—a progressive and potentially fatal disorder in which abnormal proteins build up in nerves and organs such as the heart.

Diagnostics

RNA is also playing an expanding role in diagnostics. Research into liquid biopsies (which only require a sample of human body fluids, such as blood) has increasingly shown that by measuring levels of particular RNAs, many diseases can be diagnosed at an earlier stage—including cancers, neurodegenerative diseases and cardiovascular disease.

In addition to making it easier and less invasive to collect samples, RNA biomarkers can be less painful and carry fewer risks compared to traditional tissue biopsies and other more invasive collection methods such as skin, organ, or bone biopsies.

Combinations of RNA biomarkers can also be simultaneously evaluated, allowing for more confidence in the diagnosis and prediction of disease progression and prognosis.

RNA may be used for diagnostic evaluation for diseases, including genetic, acquired, infections, tumors, cancers, a variety of physiologic dysfunctions, physiologic decline, functional changes related to environmental exposures, changes due to medication therapies or treatments. Thus, RNA must be collected and stabilized for evaluation, which can include high throughput diagnostic techniques. The selected sample furthermore once stable can be further evaluated by a variety of methods and replicated or used for downstream processing. Solutions that stabilize in a non-toxic form allow for great flexibility in diagnosis, and modification for potential therapeutic applications.

Cell Cultures

Advances in cell culture technology, including culture media, culture vessels, and culture techniques, have enabled in vitro reproduction of in vivo characteristics and functions of cells, tissues, and organs. Stabilization of RNA during the process further contributes to downstream uses of RNA for cell culture technology and subsequent product development and application.

RNA's wide range of capabilities, as well as having a simple molecular sequence that can easily be read by researchers, has made it an extremely useful tool in the development of recent biomedical technologies—including CRISPR gene editing.

Needs for Improved Stabilizing Technologies

A need exists for a composition that can reduce the degradation of mRNA in vaccines.

A need exists for a composition that can reduce the degradation of RNA in therapeutics, research and development, cell cultures, basic biological research, and molecular biology.

A need exists for a composition that can reduce the degradation of RNA in applications such as drug discovery and regenerative medicine, isolating cells from tissue and maintaining, proliferating, and/or differentiating the cells in a culture vessel containing medium.

A need further exists for solutions that can preserve and protect RNA content in solution for storage and transportation at elevated temperatures. It is highly desirable to utilize a reliable method for delivery of stable verifiably intact nucleic acid components while reducing reliance on refrigeration.

BRIEF SUMMARY

The disclosed technology includes a solution for stabilizing nucleic acids. The solution includes a chelating agent, a buffering agent, and a salt. The solution is configured to protect nucleic acid, including RNA and RNA species such as mRNA, added to the solution and prevents degradation of the nucleic acid for a duration of 1 to 180 days over a temperature range of −20 degrees C. to +38 degrees C.

The disclosed technology includes a solution for stabilizing an injectable RNA-based vaccine. The solution is safe for injection into mammals and includes a chelating agent, a buffering agent, and a salt. The solution is configured to protect an injectable RNA-based vaccine added to the solution. The solution prevents degradation of the injectable RNA-based vaccine for a duration of 1 to 180 days over a temperature range of −20 degrees C. to +38 degrees C.

The disclosed technology includes a method of manufacturing a solution for stabilizing and storing nucleic acids. The method includes preparing a solution, the solution comprises a chelating agent, a buffering agent, and a salt. The method can include configuring concentrations of the chelating agent, buffering agent, and salt for final molarities prior to the addition of a nucleic acid. The solution is configured to protect nucleic acid added to the solution and prevents degradation of the nucleic acid for a duration of 1 to 180 days over a temperature range of −20 degrees C. to +38 degrees C.

The disclosed technology includes a method of manufacturing a solution for stabilizing and storing an injectable RNA-based vaccine. The method includes preparing a solution, the solution comprises a chelating agent, a buffering agent, and a salt. The method includes configuring concentrations of the chelating agent, buffering agent, and salt for final molarities prior to the addition of an RNA-based vaccine. The solution is configured to protect the RNA-based vaccine added to the solution and prevents degradation of the RNA-based vaccine for a duration of 1 to 180 days over a temperature range of −20 degrees C. to +38 degrees C. The method can include adding an mRNA vaccine to the solution.

Other implementations, features, and aspects of the disclosed technology are described in detail herein and are considered a part of the claimed disclosed technology.

BRIEF DESCRIPTION OF THE FIGURES

Reference will now be made to the accompanying figures and flow diagrams, which are not necessarily drawn to scale, and wherein:

FIG. 14 is a flow-diagram for preparing a vaccine solution, according to certain implementations of the disclosed technology.

DETAILED DESCRIPTION

Figure 1A:
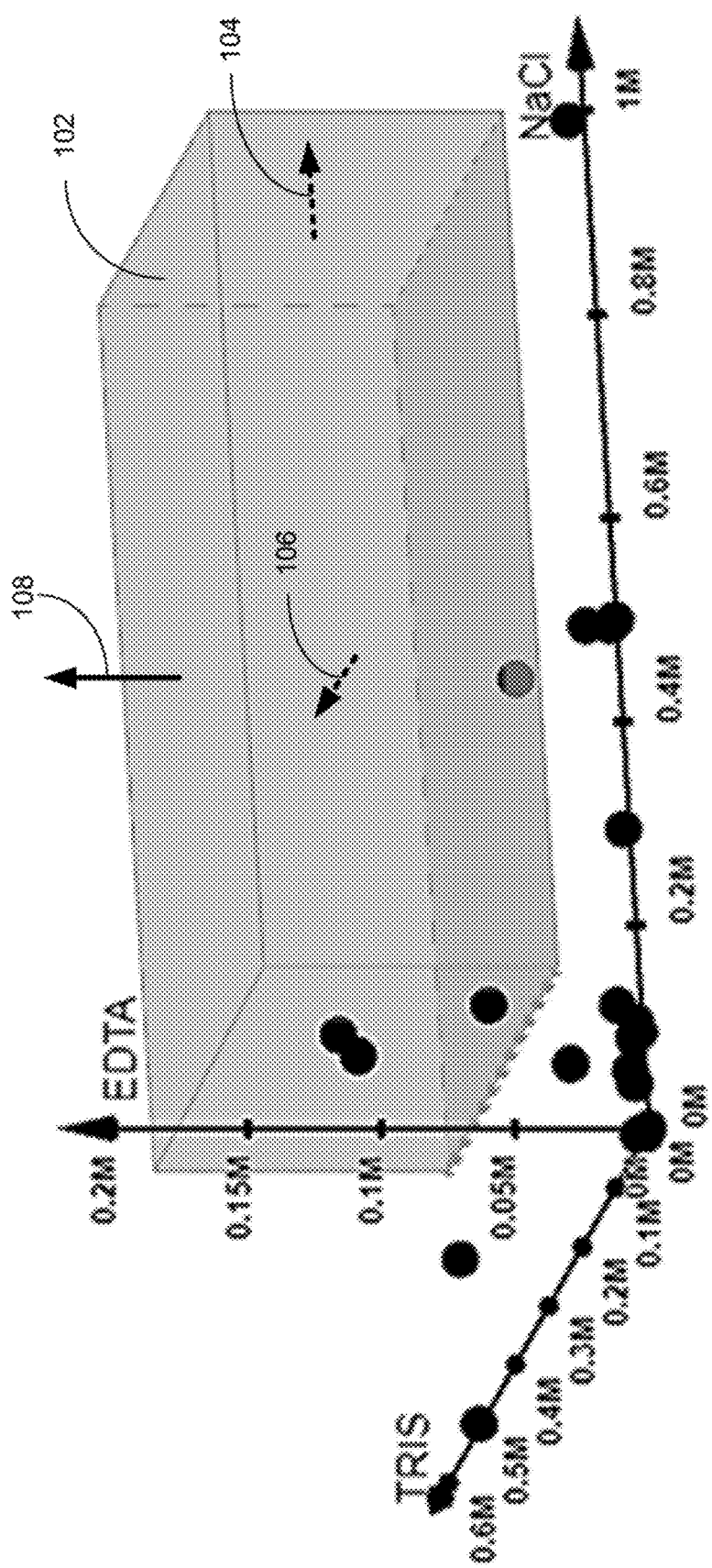
FIG. 1A is a 3-dimensional (3D) representation of component ranges of a nucleic acid preserving solution relative to previous solutions (black dots), which are not within the ranges utilized in the disclosed technology.

The disclosed technology relates to solutions and methods of manufacture for preserving and protecting nucleic acid, and specifically, the ribonucleic acid (RNA) content in a solution that allows for storage and transportation at a temperature range of −20 to 38 degrees C. and that is safe as a delivery solution into animals and humans.

As discussed in the background section above, it is essential to stabilize intact functional nucleic acids including DNA and RNA species for use in vaccines, therapeutics, and diagnostics in a manner that prevents degradation during manufacturing, storage, transport, and application. To minimize degradation of nucleic acid in biological samples, it is standard practice to maintain constructs with nucleic acids (RNA and DNA) by keeping the sample frozen in storage (−80° C. to −20° C.). The costs, logistics and infrastructure needed to ensure products are maintained at low temperatures during manufacturing, transport to medical facilities, and stored under optimal conditions prior to use, poses significant challenges and risks, especially in large-scale and population-based treatment applications. It is highly desirable to utilize a reliable method for delivery of stable verifiably intact nucleic acid components (including RNA species) and to reduce or eliminate the requirement for refrigeration for protection/preservation of the nucleic acid components.

Multiple methods have been described in the literature and are currently available for short and long-term storage of DNA. However, far fewer solutions are available for RNA preservation at ambient temperatures, and they are not amenable broadly to be used as a delivery component for safe use in humans and animals, specifically in vaccine delivery and therapeutic applications. Certain implementations of the disclosed technology may be used to solve such issues and may be used to advance nucleic acid stabilization in the fields of mRNA vaccines, diagnostic technology, drug development, and/or RNA therapies. Certain implementations of the disclosed technology may enable the preservation of nucleic acid species for manufacturing, storage, transport, and/or application thereof.

The disclosed technology includes chemical composition embodiments that allow RNA (and/or other nucleic acids) to be used for applications such as vaccines, therapeutics, and diagnostics. Certain solution components and concentrations disclosed herein allow RNA (and/or other nucleic acids) to remain stable at an extended range of temperatures for periods greater than previously achievable.

Certain exemplary implementations of the disclosed technology can include a solution made from a combination of a chelating agent, a buffering agent, and a hypertonic salt solution to prevent degradation of RNA and related species.

Certain implementations of the disclosed solution may be configured for stabilizing an injectable RNA-based vaccine that is added to the solution. Accordingly, the components of the stabilizing solution disclosed herein (including the chelating agent, buffering agent, and hypertonic salt) may be selected so that the solution is safe for injection into mammals.

According to certain exemplary embodiments of the disclosed technology, the chelating agent can include ethylenediaminetetraacetic acid (EDTA, also know as edetate calcium disodium, calcium disodium versenate). EDTA has been used for clinical applications including treatment of heavy metal toxicity. Clinical doses up to 1000 mg/m$^2$ in adults (average 1.7 m$^2$=1.7 grams) and up to 50 mg/kg-day in children have been safely used.

Certain example embodiments of the disclosed solution include molar ranges of EDTA from 0.026 molar to 1 molar solutions. This range of EDTA corresponds to a low value of 0.0076 grams/ml to a high value of 0.29 grams/ml. At the highest concentration, 5 ml of solution can be safely injected (1.3 grams). In certain cases, dosages of the solution disclosed herein containing EDTA may be adjusted based on clinical conditions and indications.

According to certain exemplary embodiments of the disclosed technology, the buffering agent can include tris (hydroxymethyl)aminomethane (TRIS). TRIS is commercially available and known as other brand and/or generic names including THAM. TRIS-based solutions can be used as a parenteral systemic alkalizer and fluid replenisher for conditions including metabolic alkylosis. Doses up to 500 mg/kg weight have been clinically used with doses in the 3.6 grams/50 kg body weight well tolerated.

Certain example embodiments of the disclosed solution include molar ranges of TRIS from 0.001 molar to 3 molar solutions. This range of TRIS corresponds to a low value of 0.00012 grams/ml to a high value of 0.36 grams/ml. At the highest concentration, 10 ml of solution can be safely injected (3.6 grams). In certain cases, dosages of the solution disclosed herein containing TRIS may be adjusted based on clinical conditions and indications.

According to certain exemplary embodiments of the disclosed technology, the salt can include NaCl having a molarity in the range of 0.15 m to 3 m. In certain implementations of the disclosed technology, the salt may be hypertonic in solution.

In accordance with certain exemplary embodiments of the disclosed technology, other components may be added to the disclosed solution, for example, to further optimize the solution for a particular application, and/or to further extend the preservation period of a nucleic acid added to the solution.

Reference will now be made to the accompanying figures and flow diagrams, which are not necessarily drawn to scale.

FIG. 1A is a 3-dimensional (3D) representation of example (truncated) component ranges 102 of a nucleic acid preserving solution relative to previous solutions (black dots), in accordance with certain implementations of the disclosed technology. This 3D representation depicts example molar concentration ranges of three example components of the nucleic acid preserving solution, which can include a salt (NaCl), a buffering agent (TRIS), and a chelating agent (EDTA). The previous solutions (represented by the black dots) do not fall within the component ranges 102 of the disclosed technology. This non-overlap of the disclosed technology with previous solutions is clearly illustrated in FIG. 1D.

One example embodiment as depicted in FIG. 1A, the solution, may include salt (such as NaCl) having a molarity (moles of a solute per liters of a solution) that can range from about 0.15M to about 1.0M. However, as indicated by the arrow 104, the upper range of the salt concentration in the solution may be extended up to about 3.0M.

One example embodiment, as depicted in FIG. 1A, the solution may include a buffering agent (such as TRIS) having a molarity that can range from about 0.001M to about 0.33M. However, as indicated by the arrows 106, the upper range of the buffering agent concentration in the solution may be extended up to about 3.0M.

One example embodiment of the solution, as depicted in FIG. 1A, may include the chelating agent (such as EDTA) having a molarity that can range from about 0.0.026M to about 0.13M. However, as indicated by the arrow 108, the upper range of the chelating agent concentration in the solution may be extended up 1.0M.

Figure 1B:
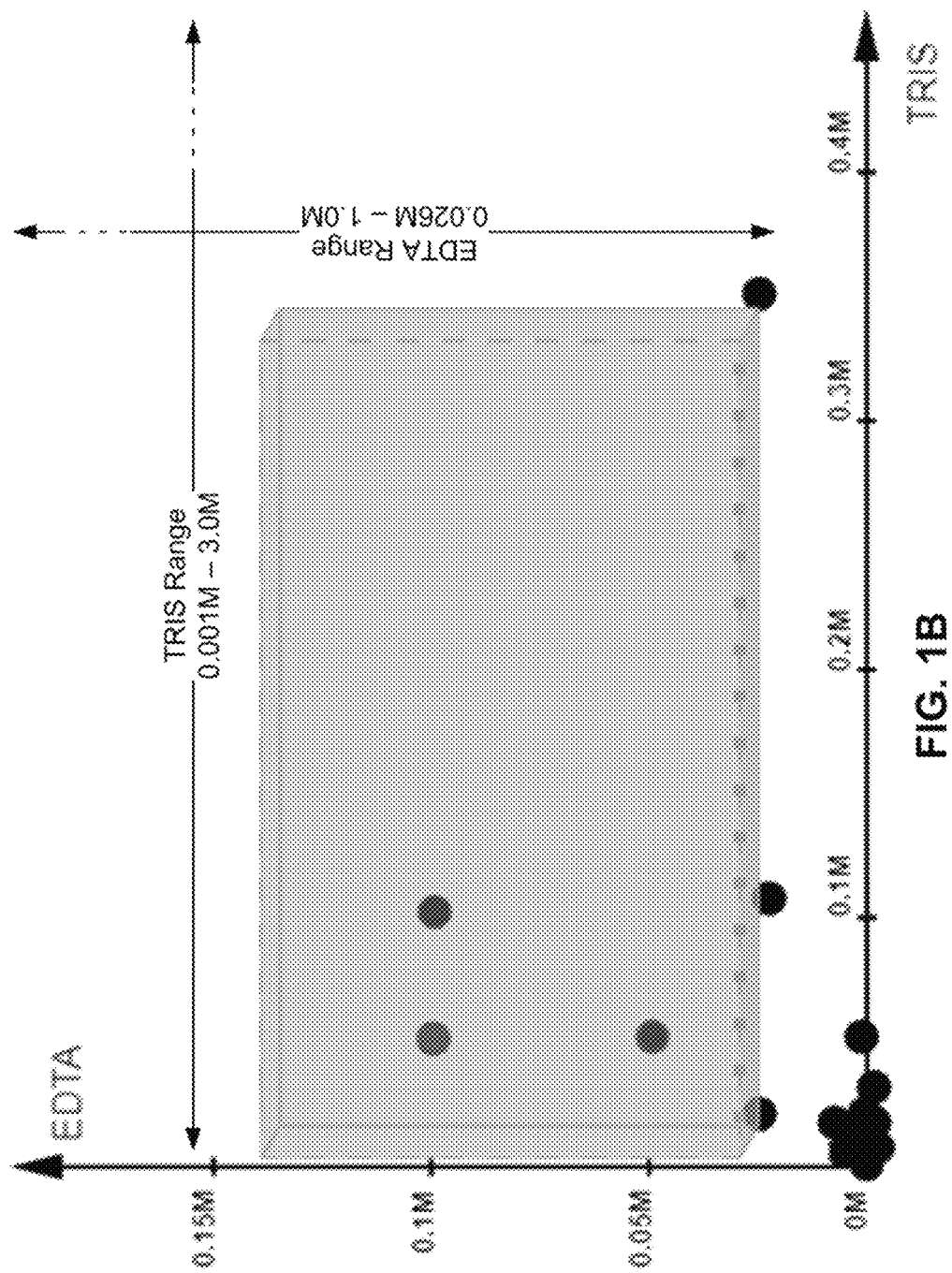
FIG. 1B is a rotated view of the 3D representation shown in FIG. 1A to illustrate TRIS and EDTA component ranges relative to the previous solutions, in accordance with certain implementations of the disclosed technology.

FIG. 1B is a rotated view of the 3D representation shown in FIG. 1A to illustrate TRIS and EDTA component ranges relative to the previous solutions, in accordance with certain implementations of the disclosed technology. As indicated by the dotted arrows, the upper ranges of the TRIS and/or the EDTA molar concentrations may be extended beyond the exemplary ranges (indicated by the box) to higher values.

Figure 1C:
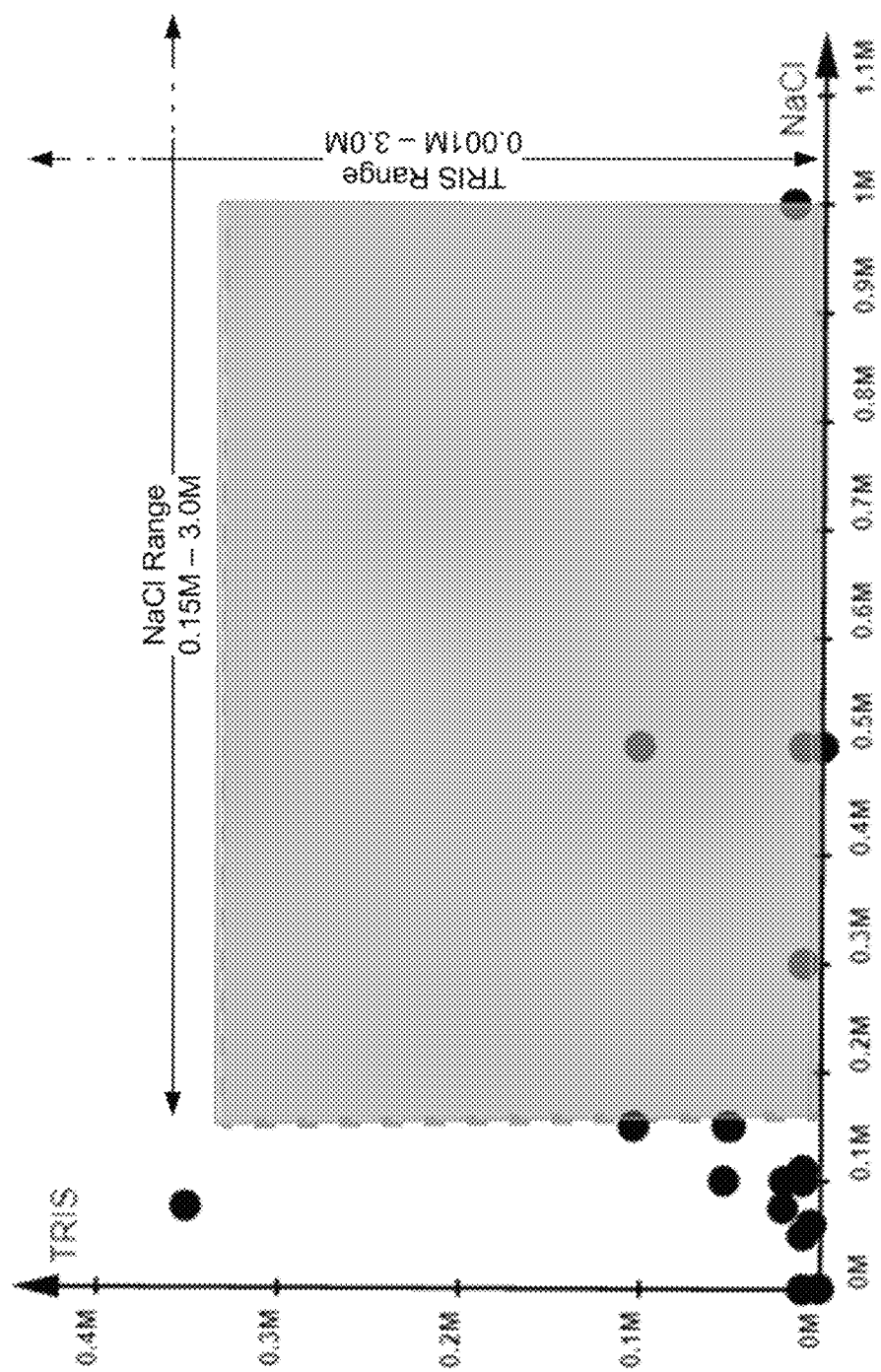
FIG. 1C is a rotated view of the 3D representation shown in FIG. 1A to illustrate TRIS and salt (NaCl) component ranges relative to the previous solutions, in accordance with certain implementations of the disclosed technology.

FIG. 1C is a rotated view of the 3D representation shown in FIG. 1A to illustrate TRIS and salt (NaCl) component ranges relative to the previous solutions, in accordance with certain implementations of the disclosed technology. As indicated by the dotted arrows, the upper ranges of the TRIS and/or the NaCl molar concentrations may be extended beyond the exemplary ranges (indicated by the box) to higher values.

Figure 1D:
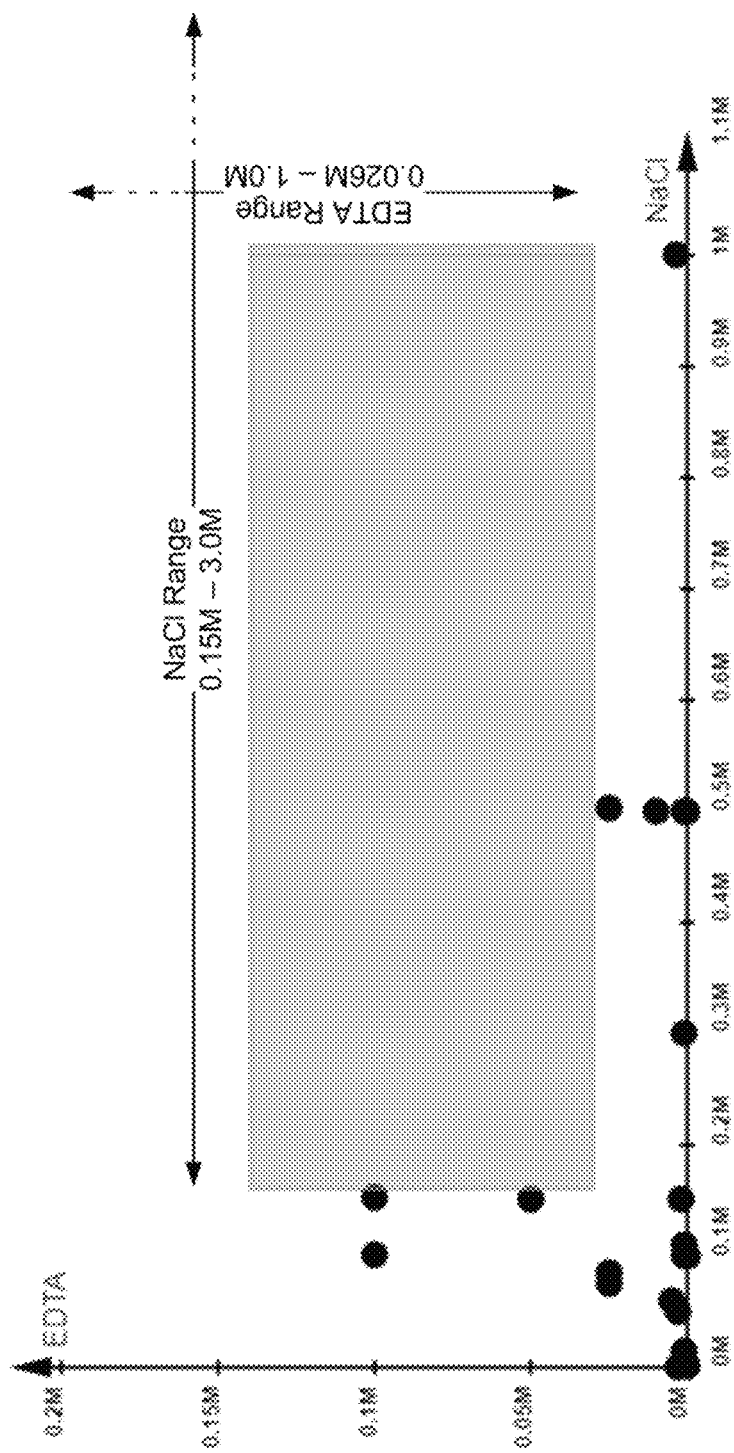
FIG. 1D is a rotated view of the 3D representation shown in FIG. 1A to illustrate ETDA and salt (NaCl) component ranges relative to the previous solutions with no overlap, in accordance with certain implementations of the disclosed technology.

FIG. 1D is a rotated view of the 3D representation shown in FIG. 1A to illustrate ETDA and salt (NaCl) component ranges relative to the previous solutions with no overlap, in accordance with certain implementations of the disclosed technology. As indicated by the dotted arrows, the upper ranges of the EDTA and/or the NaCl molar concentrations may be extended beyond the exemplary ranges (indicated by the box) to higher values.

As mentioned above, the example molarity ranges of the NaCl, TRIS, and EDTA in solution do not overlap with any of the concentration combinations that have been previously disclosed in the literature (and represented by the black dots). FIG. 1D most clearly shows the novel claimed molar ranges of components used for the example solutions relative to the literature.

Figure 2:
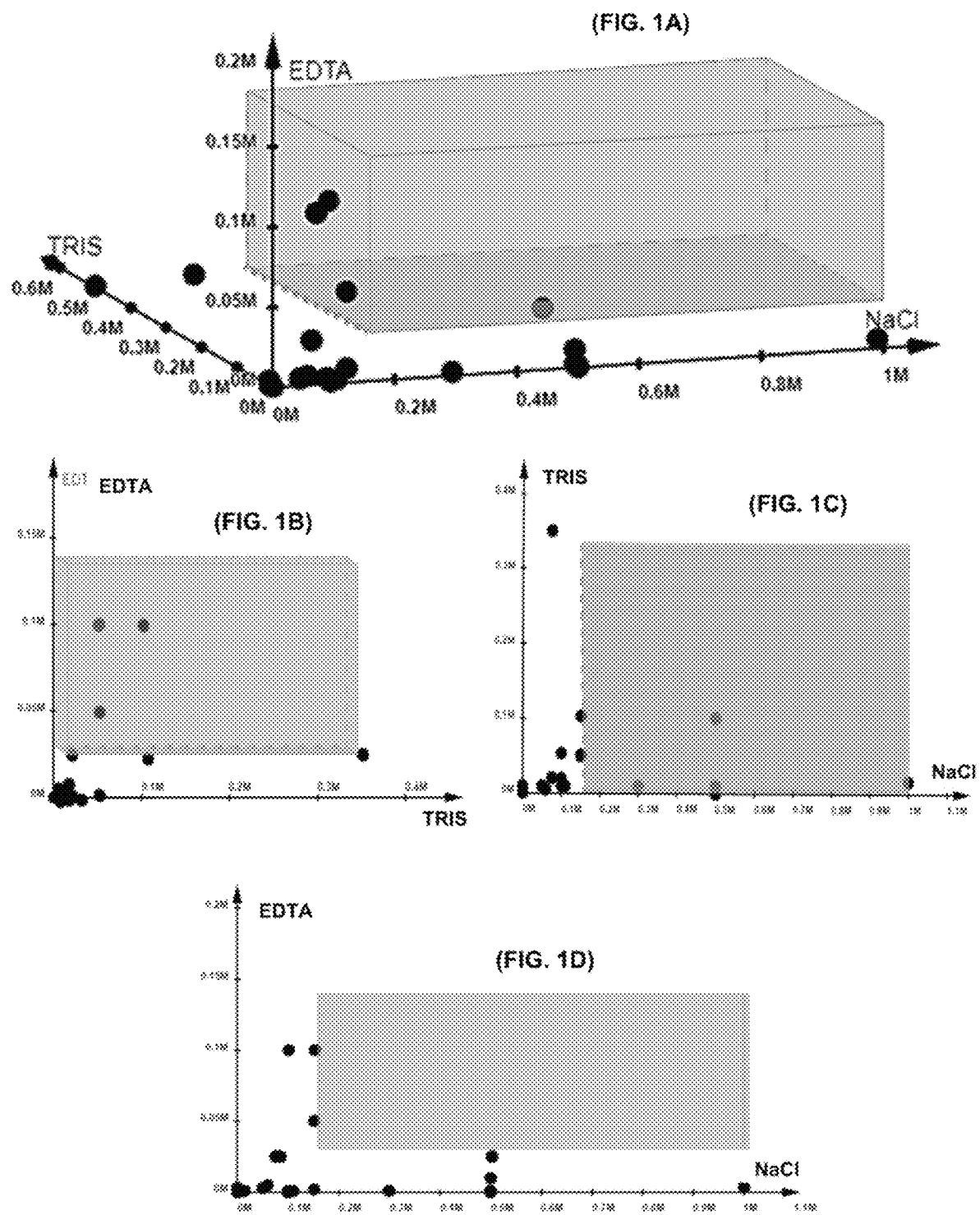
FIG. 2 is a reproduction of FIGS. 1A-1D on the same sheet for comparison.

FIG. 2 is a reproduction of FIGS. 1A-1D on the same sheet for comparison.

FIGS. 3-10 are charts showing experimental PCR data corresponding to nucleic acid protection/degradation for various-length and -temperature runs using certain implementations of the disclosed solutions.

Real-time PCR assays utilize fluorescence to determine an amount of target nucleic acid in a solution. The cycle threshold (CT) is defined as the number of cycles required for the fluorescent signal to cross a background level threshold. CT levels are inversely proportional to the amount of target nucleic acid in the sample (SARS-COV-2 in this experiment). The lower is the CT level, the greater the amount of target nucleic acid is in the solution. A CT of 40 or greater indicates minimal amounts of detected target nucleic acid. A CT of 45 or greater indicates that there is no detectable amount of in-tact nucleic acid left in the solution.

Figure 3:
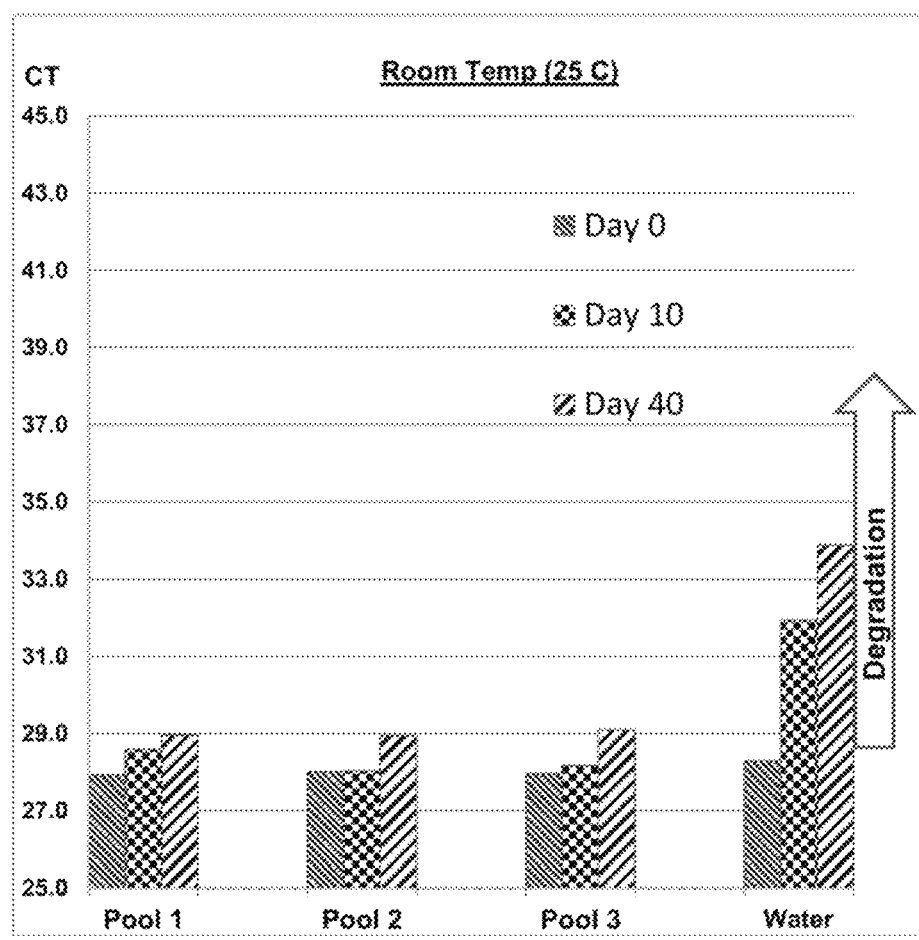
FIG. 3 is a chart summarizing experimental PCR data using 16,500 copies per ml of SARS-COV-2 for room-temperature runs (25 degrees C.) at pH=8.

FIG. 3 is a chart summarizing experimental PCR data using 16,50) copies per ml of SARS-COV-2 genomic RNA added to solutions for various-length room-temperature runs (25 degrees C.) at pH=8. In this experiment, three solution pools were prepared: Pool 1: 0.1M EDTA, 0.075M TRIS, 0.5M NaCl; Pool 2: 0.1M EDTA, 0.05M TRIS, 0.5M NaCl; Pool 3: 0.1M EDTA, 0.025M TRIS, and 0.5M NaCl. For reference, 16,500 copies per ml of the SARS-COV-2 genomic RNA were also added to water (without salt, chelating agent, or buffering agent) and tested in the incubator at 25 degrees C., as indicated in the far-right grouping. The day 10 and day 40 results show little or no degradation for Pools 1-3. However, the results indicate a degradation of the target nucleic acid in water alone at day 10 and more degradation at day 40. FIG. 3 indicates that a target nucleic acid can be protected using the disclosed solution.

Figure 4:
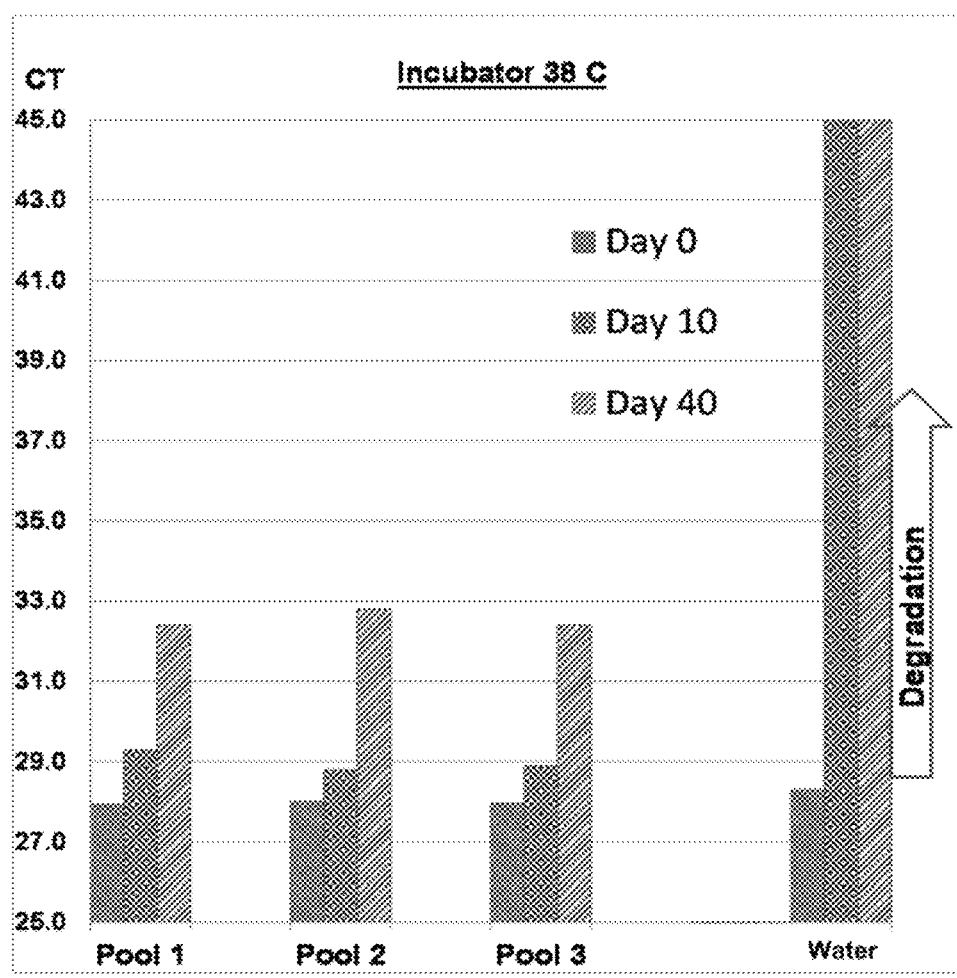
FIG. 4 is a chart summarizing experimental PCR data using 16,500 copies per ml of SARS-COV-2 for incubator runs (38 degrees C.) at pH=8.

FIG. 4 is a chart summarizing experimental PCR data using 16,500 copies per ml of SARS-COV-2 genomic RNA added to solutions for various-length runs in an incubator (38 degrees C.). In this experiment, the same pools, pH values, and water reference as described above for FIG. 3 were utilized. As in FIG. 3, the day 10 and day 40 results show little or no degradation for Pools 1-3. However, the results in FIG. 4 indicate a severe degradation of the target nucleic acid in water alone at day 10 and day 40 at the elevated temperature. FIG. 4 indicates that a target nucleic acid can be protected using the disclosed solution.

Figure 5:
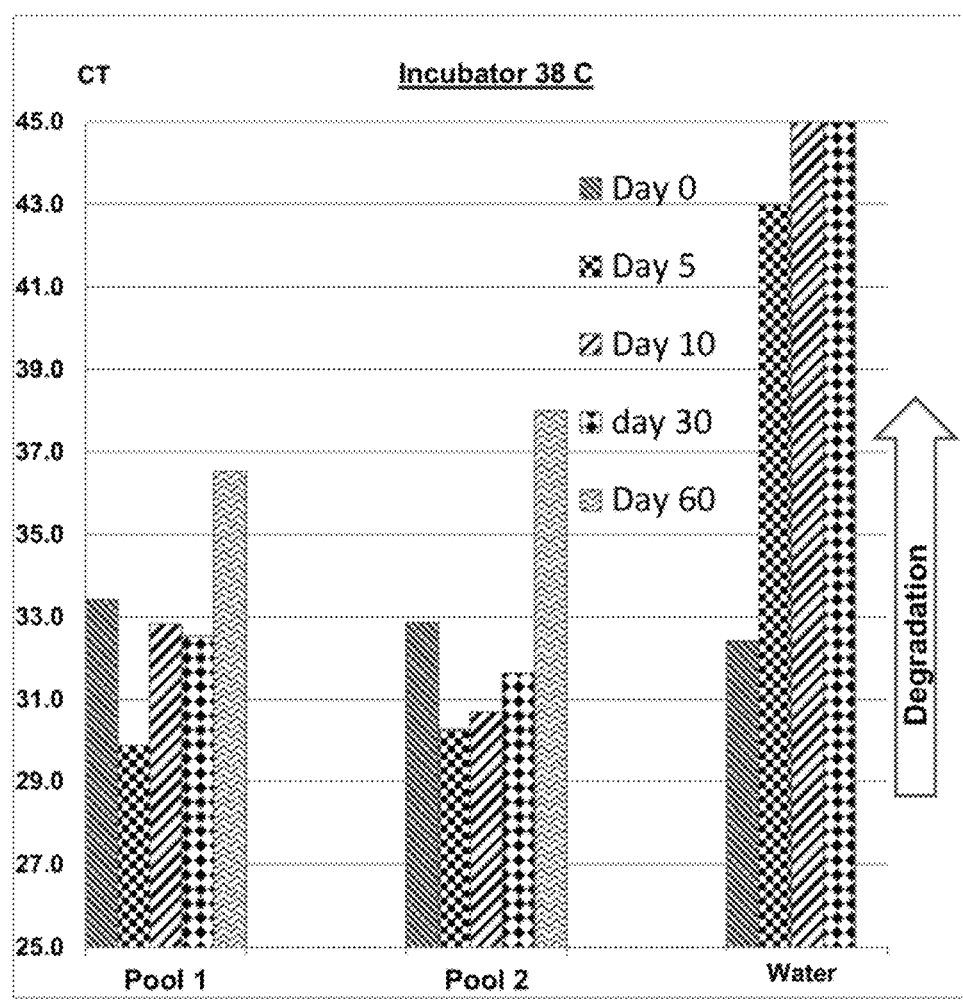
FIG. 5 is a chart summarizing experimental PCR data using 16,500 copies per ml of SARS-COV-2 for various-length incubator runs (38 degrees C.).

FIG. 5 is a chart summarizing experimental PCR data using 16,500 copies per ml of SARS-COV-2 added to a solution for various-length runs in an incubator (38 degrees C.). In this experiment, two solution pools having 0.075M EDTA, 0.075M TRIS, and 0.35M NaCl were tested, and degradation results are plotted for day 0 (baseline) through day 60 for the two pools. For reference, 16,500 copies per ml of SARS-COV-2 genomic RNA were also added to water (without salt, chelating agent, or buffering agent) and tested in the incubator at 38 degrees C., as indicated in the far-right grouping.

As indicated in FIG. 5, both Pool 1 and Pool 2 PCR tests show little (if any) degradation of the target nucleic acid at day 30 in the incubator. The target nucleic acid in the solution is still detectable after being in the incubator for 60 days. In contrast, there considerable degradation of the target nucleic acid at day 5 with no detectable amount present after day 10 for the same tests using the target nucleic acid in just water. FIG. 5 indicates that a target nucleic acid can be protected using the disclosed solution.

Figure 6:
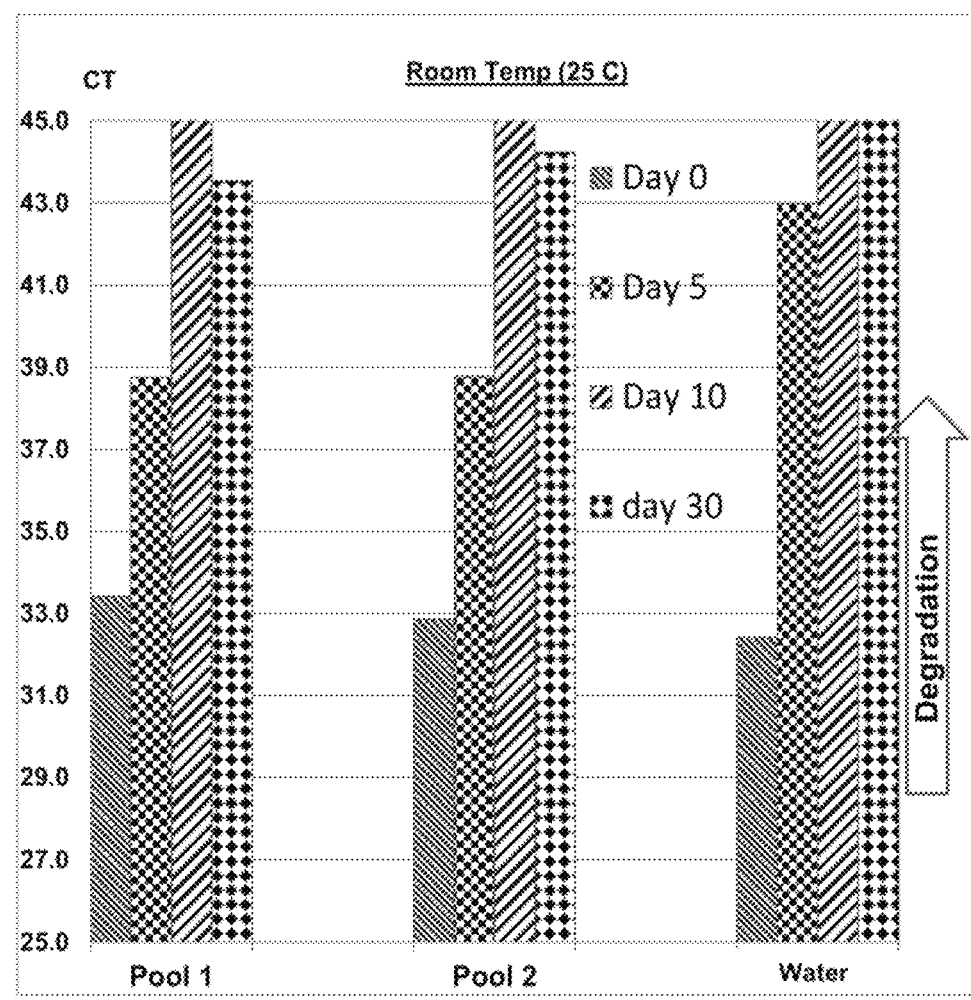
FIG. 6 is a chart summarizing experimental PCR data using 16,500 copies per ml of SARS-COV-2 for various-length room-temperature runs (25 degrees C.).
Figure 8:
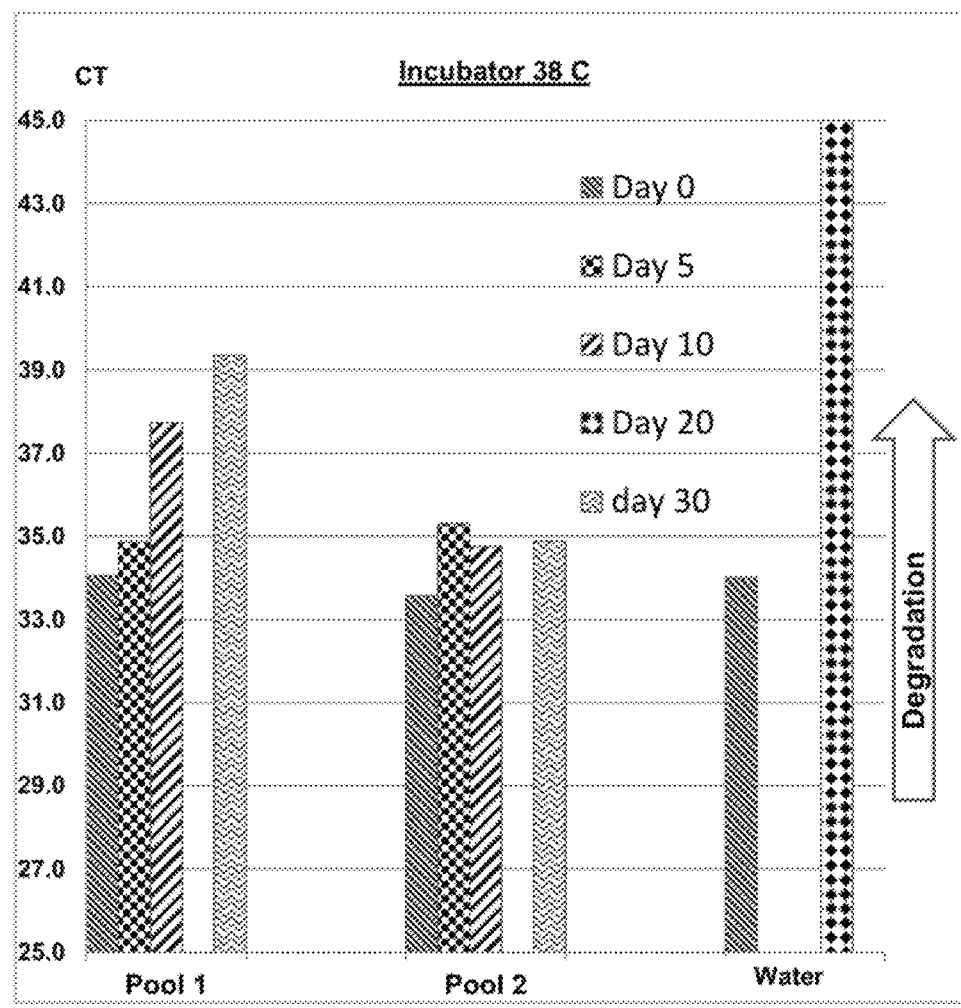
FIG. 8 is a chart summarizing experimental PCR data using 1500 copies per ml of SARS-COV-2 for various-length incubator runs (38 degrees C.).

FIG. 6 is a chart summarizing experimental PCR data using 16,500 copies per ml of SARS-COV-2 added to solutions for various-length room-temperature runs (25 degrees C.). In the experiment, two solution pools were prepared having 0.075M EDTA, 0.075M TRIS, and 0.35M NaCl. The day 5 results for the solutions (Pool 1 and Pool 2) show a slight degradation, but not as drastic degradation of the genomic RNA in water only. By comparing results summarized in FIG. 6 with those of FIG. 8, which utilized similar molar concentrations of the EDTA, TRIS, and NaCl, the ambient temperature results (FIG. 6) for day 5 and day 10 appear to have higher levels of degradation compared with the incubator runs (FIG. 8). This result and comparison indicate that there may be a complex and unexpected relationship between the solution temperature and the degradation, as it appears that the elevated temperature creates a condition in which the solution can more effectively protect the nucleic acid.

Figure 7:
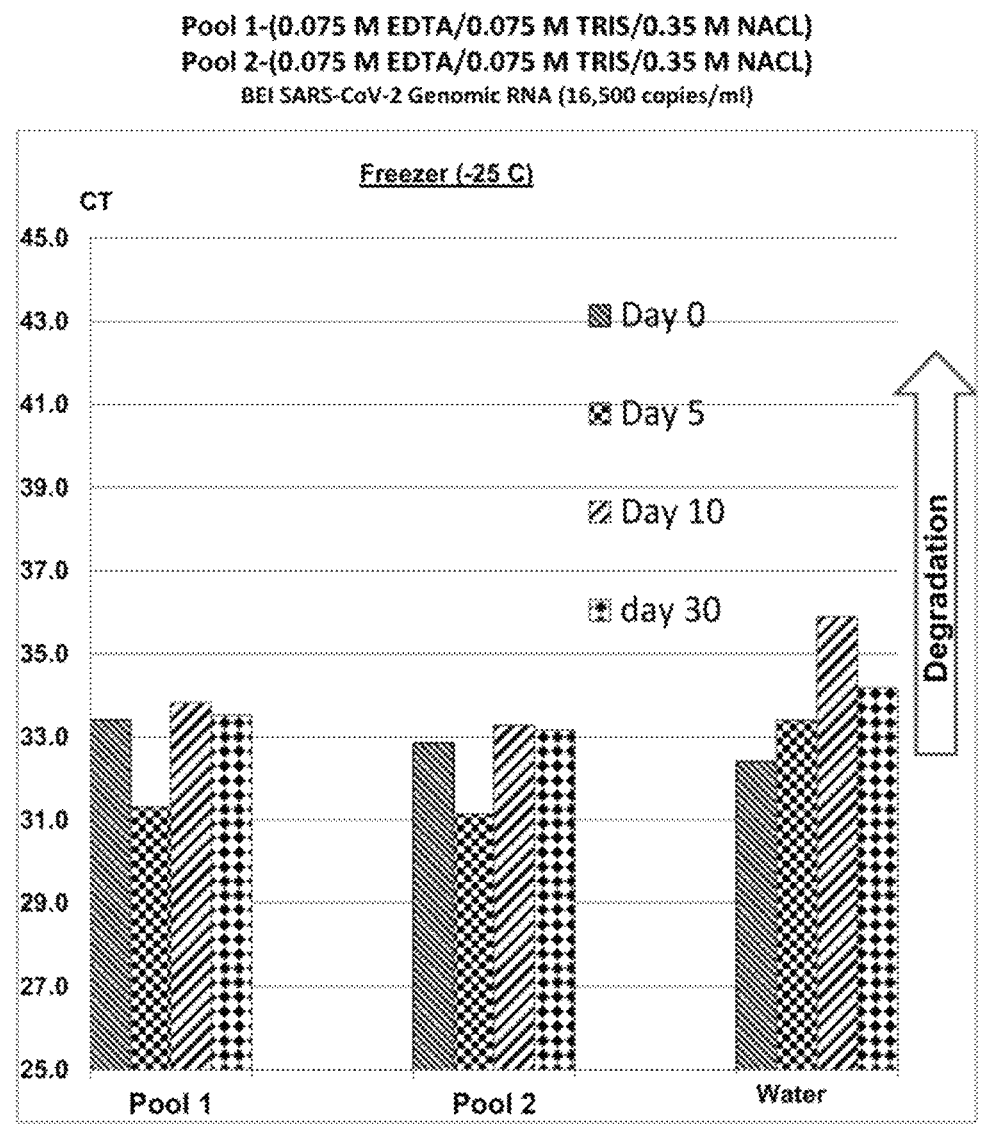
FIG. 7 is a chart summarizing experimental PCR data using 16,500 copies per ml of SARS-COV-2 for various-length freezer runs (−25 degrees C.).

FIG. 7 is a chart summarizing experimental PCR data using 16,500 copies per ml of SARS-COV-2 for various-length freezer runs (−25 degrees C.). In this experiment, two solution pools were prepared having 0.075M EDTA, 0.075M TRIS, and 0.35M NaCl. As expected, the target nucleic acid in the water-only reference pool showed a slight degradation compared to the other two pools that utilized an embodiment of the disclosed solution, but the freezer's cold temperatures may have had an influence in extending the preservation time-period for the target nucleic acid in the water.

FIG. 8 is a chart summarizing experimental PCR data using 1500 copies per ml of SARS-COV-2 genomic RNA added to solutions for various-length incubator runs at 38 degrees C. In the experiment, two solution pools were prepared having 0.075M EDTA, 0.075M TRIS, and 0.35M NaCl. This experiment utilized a relatively low number (1500) of genomic RNA copies added to the solution to essentially increase the sensitivity of degradation detection. The Pool 1 and Pool 2 samples were tested at day 0, 5, 10, and 30, while the reference (water) was tested at day 1 and day 20. As expected, there was no detectable amount of the genomic RNA in the water sample after day 20, but there were still detectable amounts in Pool 1 and Pool 2, even after day 30, indicating that certain implementations of the disclosed solution can effectively protect nucleic acid when it is added to the solution.

Figure 9:
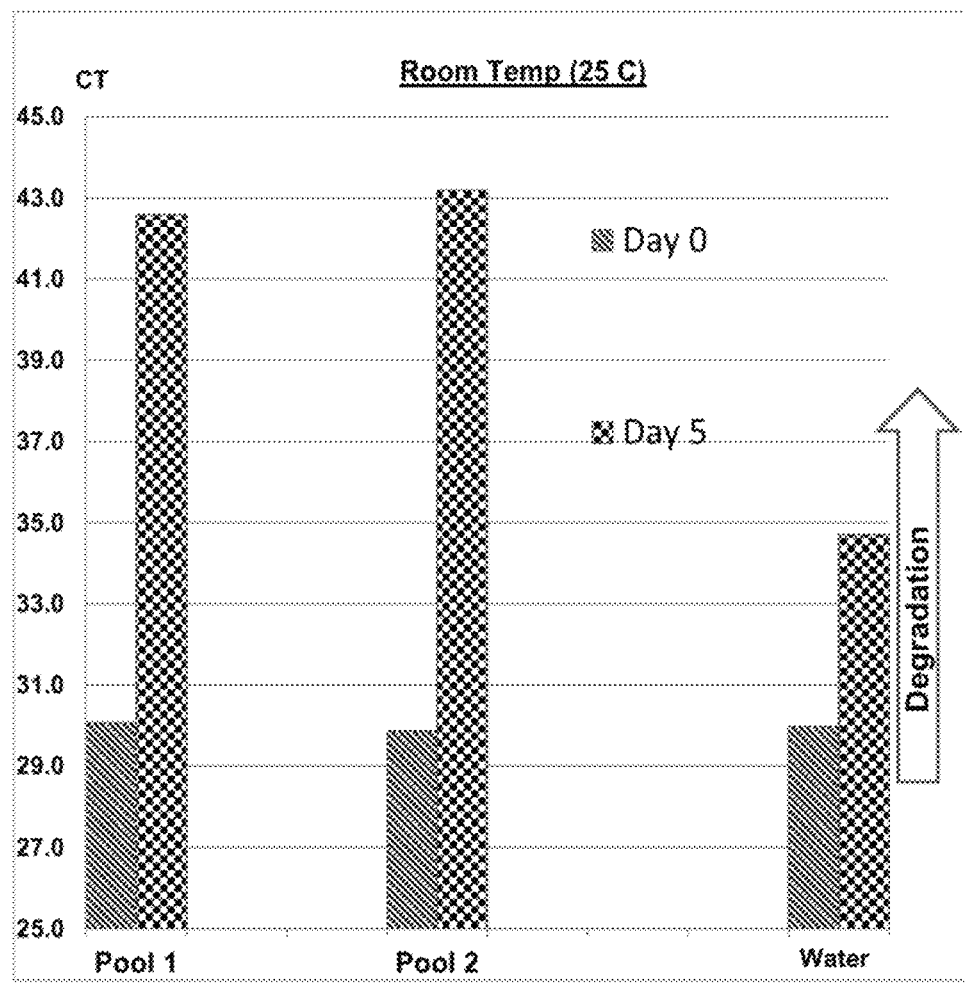
FIG. 9 is a chart summarizing experimental PCR data using 16,500 copies per ml of SARS-COV-2 for various-length room-temperature runs (25 degrees C.) with added dextrose.

FIG. 9 is a chart summarizing experimental PCR data using 16,50) copies per ml of SARS-COV-2 for various-length room-temperature runs (25 degrees C.) with dextrose. In the experiment, two solution pools were prepared having 0.1M EDTA, 0.1M TRIS, 0.5M NaCl, and 0.1M dextrose. The results indicate that dextrose may contribute detrimentally to the degradation of the nucleic acid.

Figure 10:
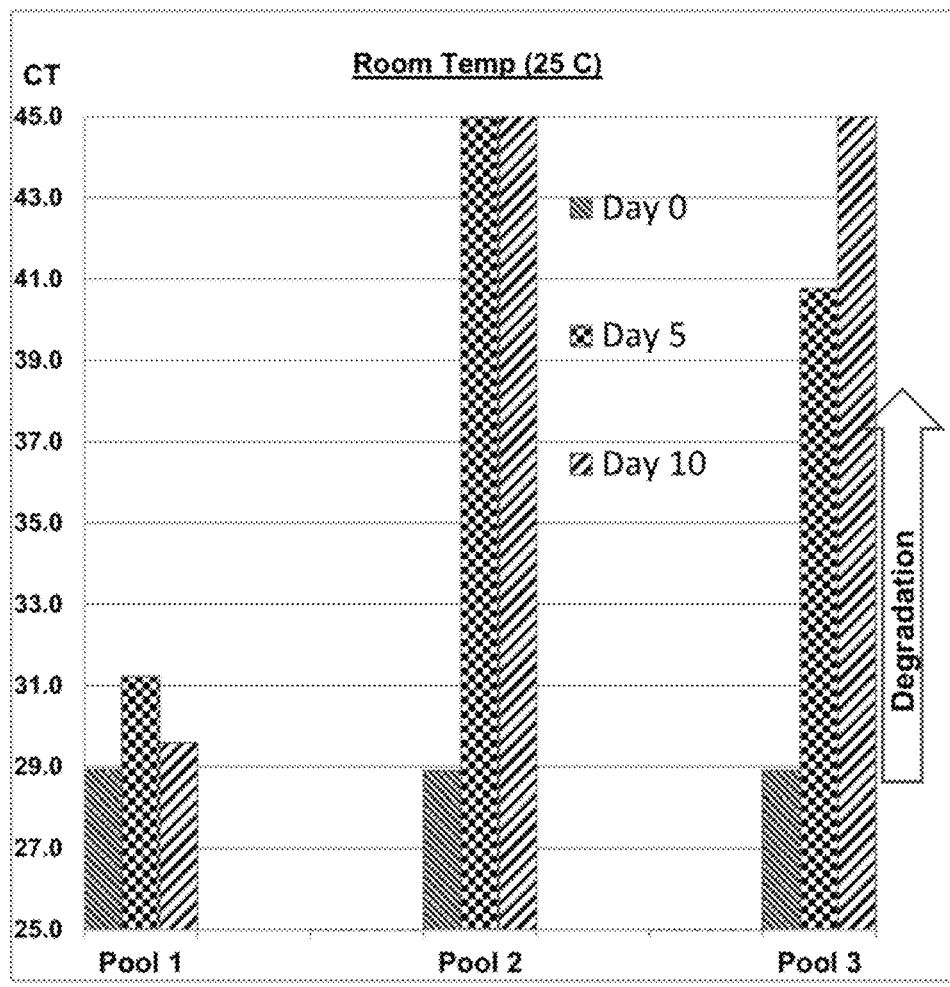
FIG. 10 is a chart summarizing experimental PCR data using 16,500 copies per ml of SARS-COV-2 for various-length room-temperature runs (25 degrees C.) with pH=8 for pool 1, pH=5 for pools 2 and 3, and dextrose added to pool 2.

FIG. 10 is a chart summarizing experimental PCR data using 16,500 copies per ml of SARS-COV-2 for various-length room-temperature runs (25 degrees C.) with pH=8 for pool 1, pH=5 for pools 2 and 3, and dextrose added to pool 2. The Pool 2 results with the added dextrose shows the most rapid degradation of the nucleic acid. The results further indicate that the acidic environment (pH=5) may contribute detrimentally to the degradation of the nucleic acid compared with the slightly alkaline environment (pH=8).

Figure 11:
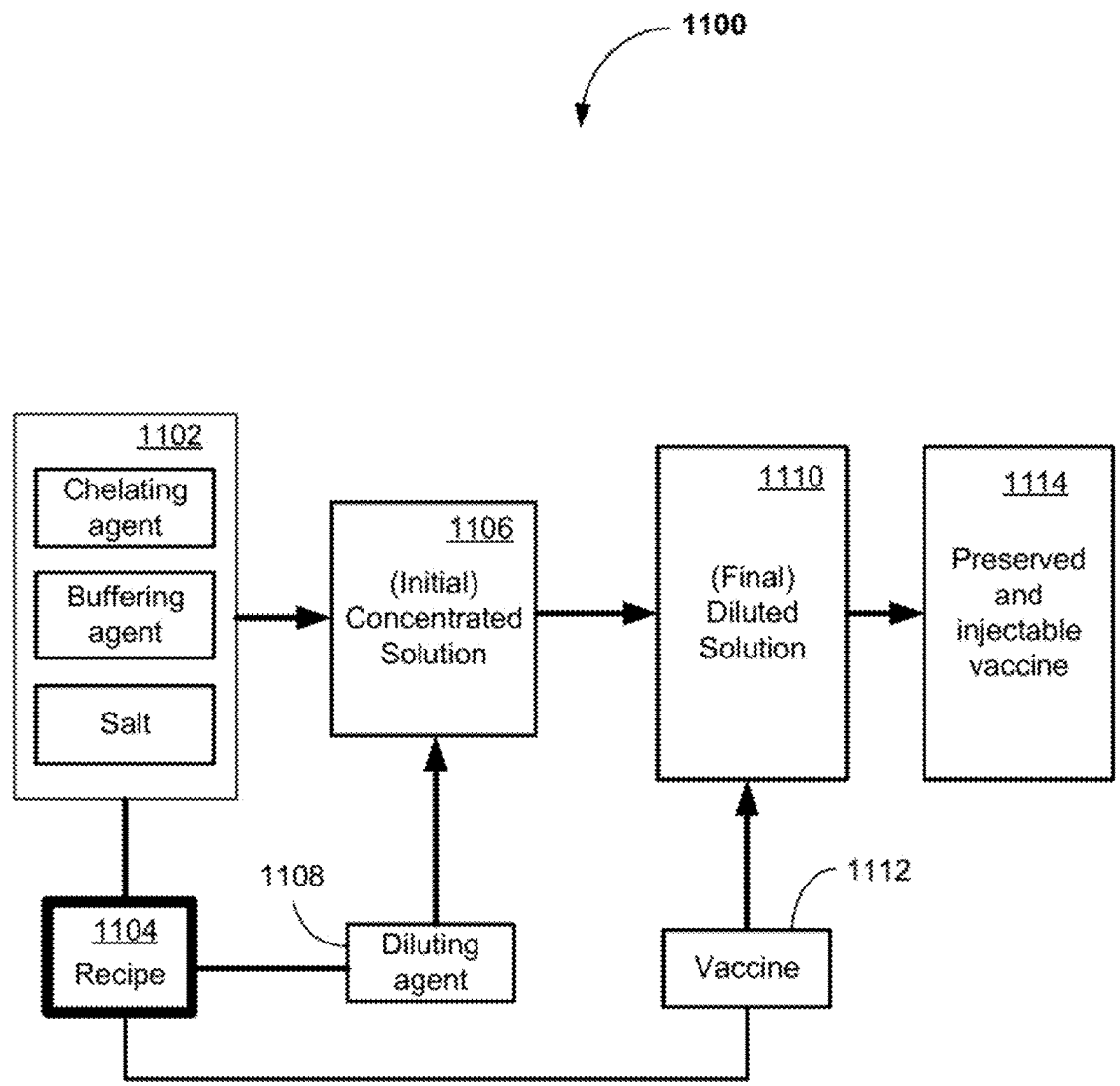
FIG. 11 is a block diagram for preparing initial concentrated solution, diluting the solution to make a final value, adding a vaccine to the solution, and preserving the injectable vaccine in the final concentration of the solution.

FIG. 11 is a block diagram of a method 1100 for preserving an injectable vaccine. The method 1100 may include combining components 1102 according to a recipe 1104 to produce a concentrated solution 1106. The components can include a chelating agent, a buffering agent, and a salt. The method 1100) can include adding a diluting agent 1108 to the concentrated solution 1106 to produce a diluted solution 1110. The method 1100 may include adding a vaccine 1112 to the diluted solution 1110 to produce a preserved and injectable vaccine 1114.

Certain exemplary embodiments may utilize the recipe 1104 for one or more of the steps, including the preparation of the concentrated solution 1106, diluting 1108 the solution to make a final value, and/or adding a vaccine 1112 to the diluted solution 1110 to make the preserved and injectable vaccine 1114. In certain implementations of the disclosed technology, the recipe 1104 may provide instructions for bypassing the step of making the (initial) concentrated solution 1106 and may utilize a diluting agent 1108 (such as purified water) when combining the components 1102 to produce the (final) solution 1110 suitable for direct addition of the vaccine 1112. Certain implementations of the disclosed technology may include adjusting the pH of the concentrated solution 1106 or the diluted solution 1110 prior to adding the vaccine 1112. According to certain implementations, the vaccine 1112 may be added to the solution at any stage or stages as needed, including stages of production of the solution, production of the vaccine, before storage, after storage, prior to transport, after transport, and/or before the end use such as injection. In certain implementations the vaccine may be added to different concentrations of the solution at any suitable stage in the production/storage/delivery/injection chain.

Figure 12:
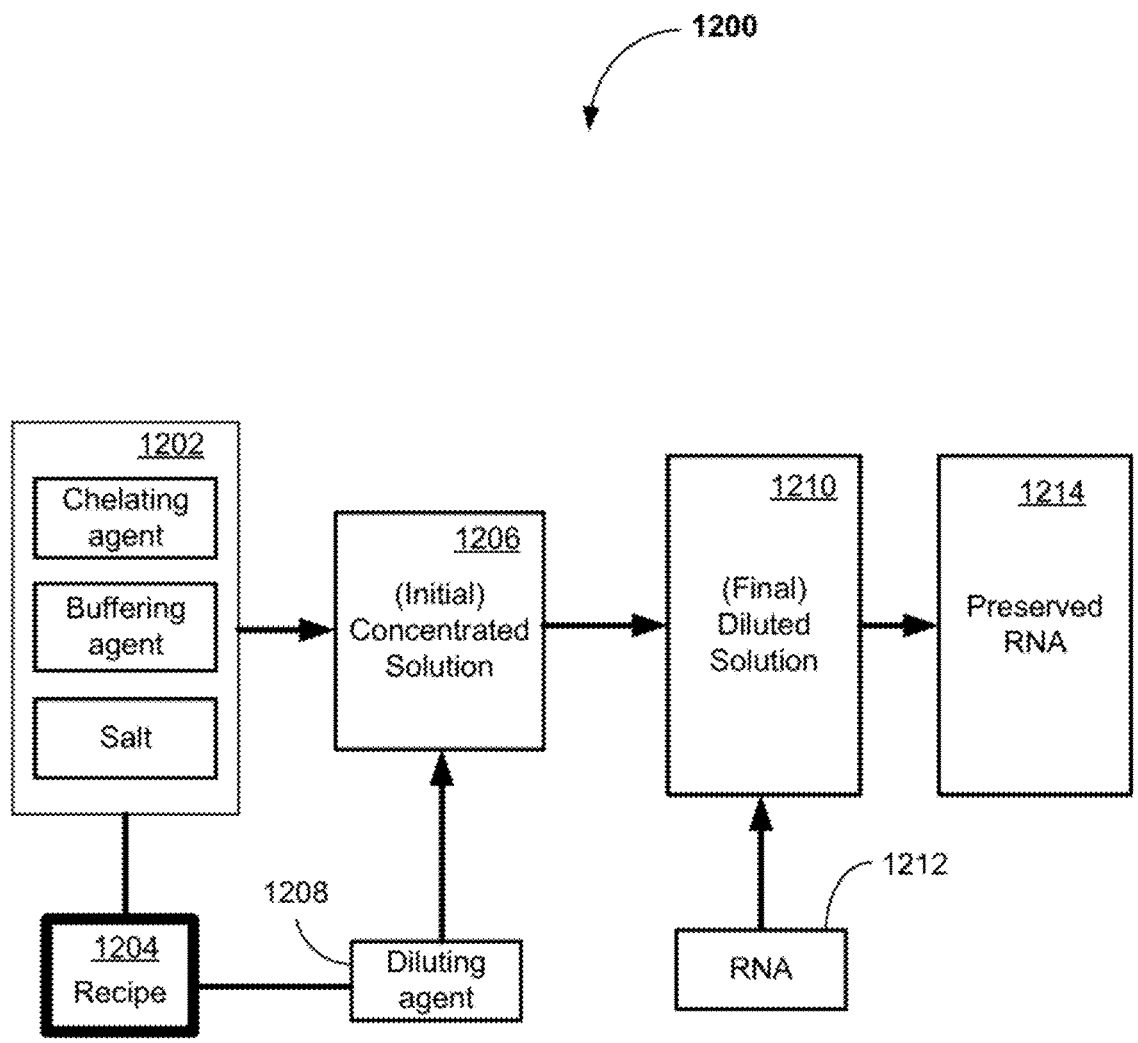
FIG. 12 is a block diagram for preparing initial concentrated solution, diluting the solution to make a final value, adding RNA to the solution, and preserving the RNA in the final concentration of the solution.

FIG. 12 is a block diagram of a method 1200 for preparing a solution to preserve RNA. The method 1200 may include combining components 1202 according to a recipe 1204 to produce a concentrated solution 1206. The components can include a chelating agent, a buffering agent, and a salt. The method 1200 can include adding a diluting agent 1208 to the concentrated solution 1206 to produce a diluted solution 1210. The method 1200 may include adding RNA 1212 to the diluted solution 1210 to preserve the RNA 1214.

Certain exemplary embodiments may utilize the recipe 1204 for one or more of the steps, including the preparation of the concentrated solution 1206, diluting 1208 the solution to make a final value, and/or adding the RNA 1212 to the diluted solution 1210 to preserve the RNA 1214. In certain implementations of the disclosed technology, the recipe 1204 may provide instructions for bypassing the step of making the (initial) concentrated solution 1206 and may utilize a diluting agent 1208 (such as purified water) when combining the components 1202 to produce the (final) solution 1210 suitable for direct addition of the RNA 1212. Certain implementations of the disclosed technology may include adjusting the pH of the concentrated solution 1206 or the diluted solution 1210 prior to adding the RNA 1212.

Figure 13:
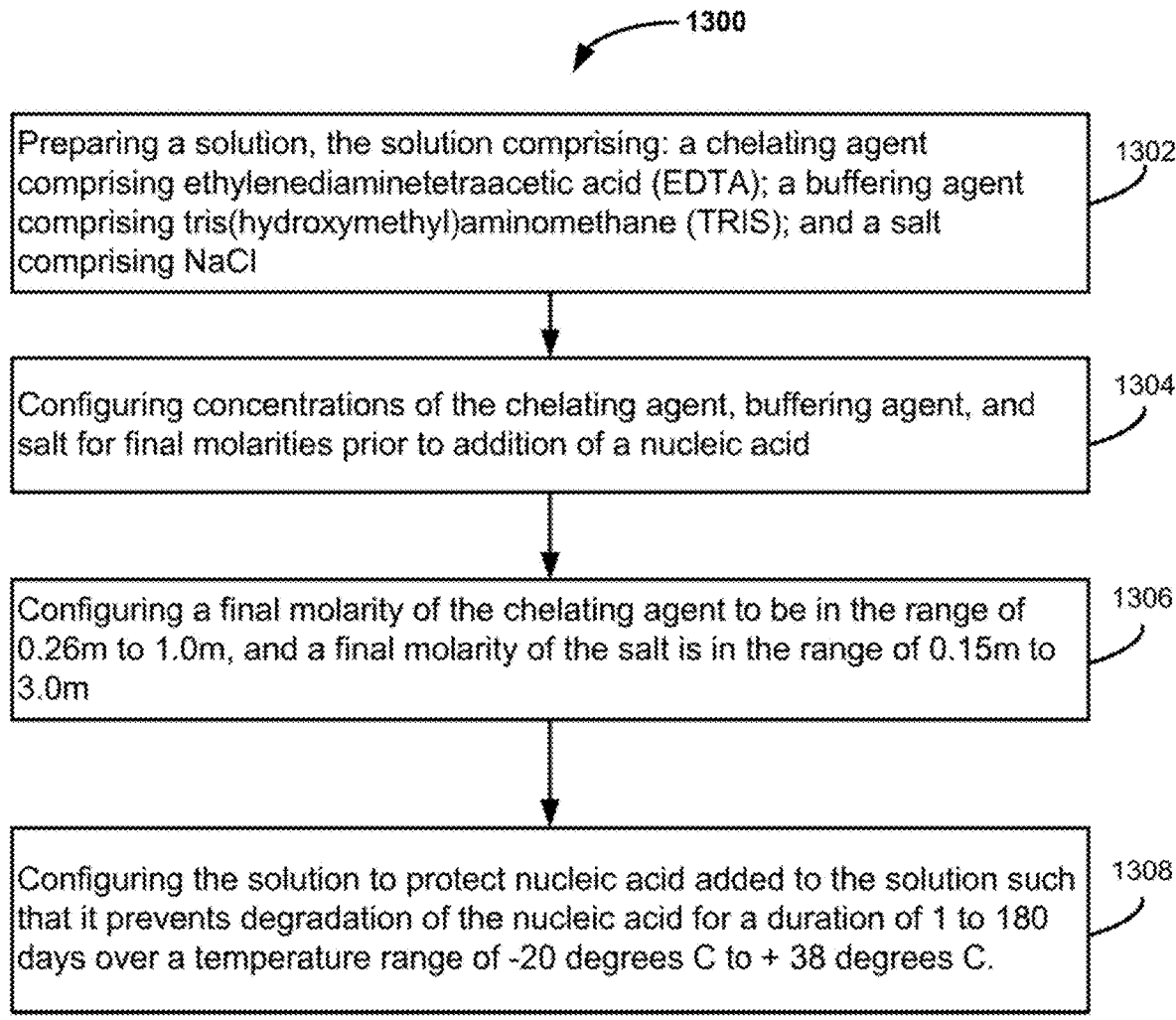
FIG. 13 is a flow-diagram for preparing a nucleic acid-preserving solution, according to certain implementations of the disclosed technology.

FIG. 13 is a flow-diagram of a method 1300 for manufacturing a nucleic acid-preserving solution, according to certain implementations of the disclosed technology. In block 1302, the method 1300 includes preparing a solution comprising: a chelating agent that can comprise ethylenediaminetetraacetic acid (EDTA); a buffering agent that can comprise tris(hydroxymethyl)aminomethane (TRIS); and a salt comprising NaCl. In block 1304 the method 1300 includes configuring concentrations of the chelating agent, buffering agent, and salt for final molarities prior to addition of a nucleic acid. In block 1306, the method 1300 includes configuring a final molarity of the chelating agent to be in the range of 0.26 m to 1.0 m and configuring a final molarity of the salt to be in the range of 0.15 m to 3.0 m. In block 1308, the method 1300 includes configuring the solution to protect nucleic acid added to the solution such that it prevents degradation of the nucleic acid for a duration of 1 to 180 days over a temperature range of −20 degrees C. to +38 degrees C.

FIG. 14 is a flow-diagram of a method 1400 for manufacturing a vaccine solution, according to certain implementations of the disclosed technology. In block 1402, the method 1400 includes preparing a solution comprising: a chelating agent comprising ethylenediaminetetraacetic acid (EDTA); a buffering agent comprising tris(hydroxymethyl)aminomethane (TRIS); and a salt comprising NaCl. In block 1404, the method 1400 can include configuring concentrations of the chelating agent, buffering agent, and salt for final molarities prior to addition of a vaccine to the solution. In block 1406, the method 1400 can include configuring a final molarity of the chelating agent to be in the range of 0.026 m to 1.0 m and configuring a final molarity of the salt to be in the range of 0.15 m to 3.0 m. In block 1408, the method 1400 includes configuring the solution so that it is safe for injection into mammals and so that it protects vaccine added to the solution and prevents degradation of the vaccine for a duration of 1 to 180 days over a temperature range of minus 20 degrees C. to +38 degrees C.

Figure 15:
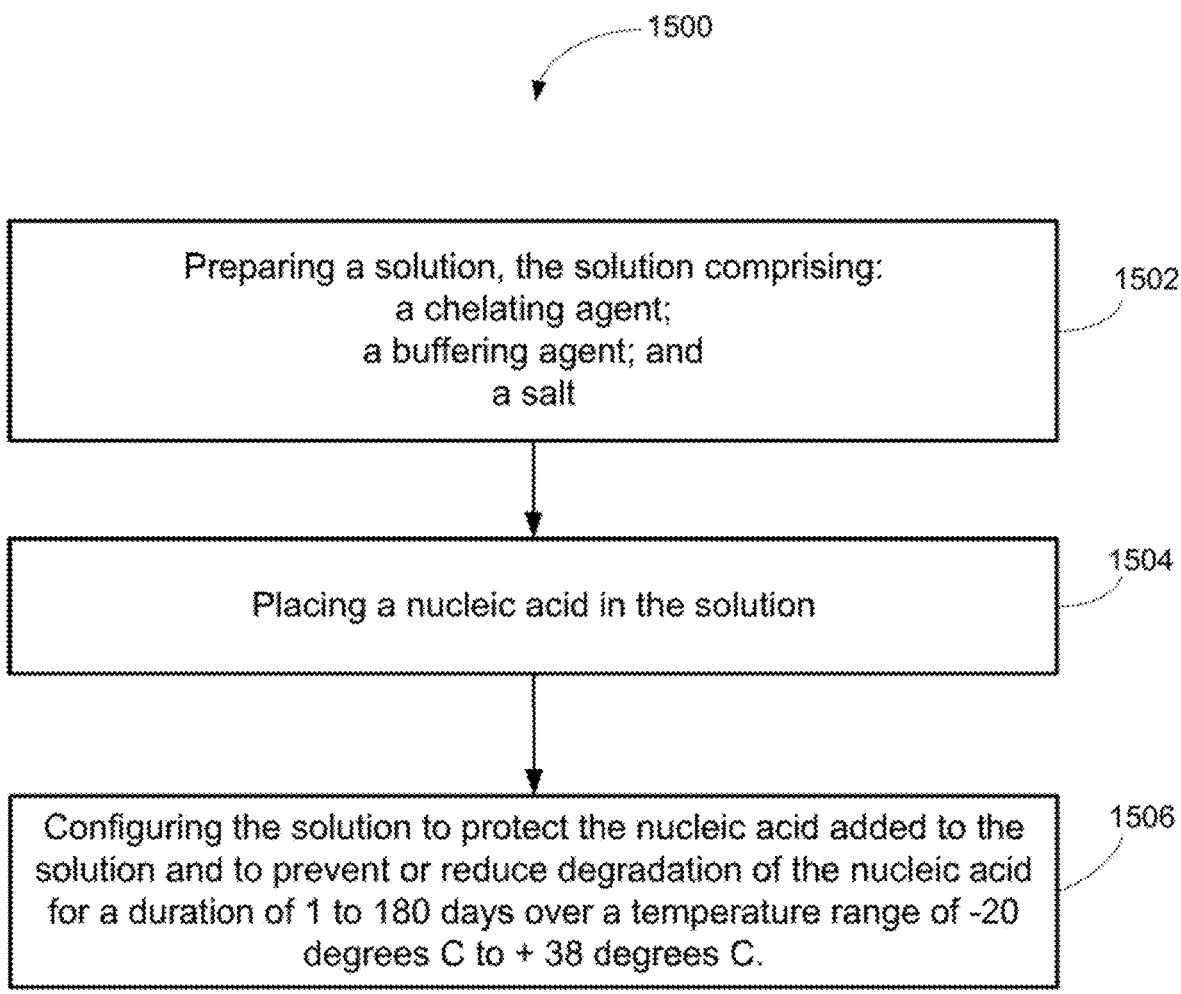
FIG. 15 is a flow-diagram for preparing a solution, according to certain implementations of the disclosed technology.

FIG. 15 is a flow-diagram of a method 1500 for preparing a solution to protect RNA added to the solution, according to certain implementations of the disclosed technology. In block 1502, the method 1500 includes preparing a solution, the solution comprising: a chelating agent; a buffering agent; and a salt. In block 1504, the method 1500 includes placing a nucleic acid in the mixture. In block 1506, the method 1500 includes configuring the solution to protect the nucleic acid added to the solution and to prevent or reduce degradation of the nucleic acid for a duration of 1 to 180 days over a temperature range of −20 degrees C. to +38 degrees C.

In accordance with certain exemplary implementations of the disclosed technology, the chelating agent can include one or more of: dimercaptosuccinic acid (DMSA); 2,3-dimercaptopropanesulfonic acid (DMPS); alpha lipoic acid (ALA); ethylenediaminetetraacetic acid (EDTA); 2,3-dimercaptopropanesulfonic acid (DMPS); thiamine tetrahydrofurfuryl disulfide (TTFD); Dimercaprol; Penicillamine; Trientine; Zinc; Deferasirox; Deferiprone; Deferoxamine; Succimer; and 1,2-cyclohexanediamine tetraacetic acid (CDTA); Dimercaprol; Penicillamine; Trientine; Zinc; Deferasirox; Deferiprone; Deferoxamine; and Succimer; diethylenetriamine pentaacetic acid (DTPA); tetraazacyclododecanetctraacetic acid (DOTA), tetraazacyclotetradecanetetraacetic acid (TETA), desferioximine, and/or chelator analogs thereof.

In certain implementations of the disclosed technology, the chelating agent can include ethylenediaminetetraacetic acid (EDTA). In certain implementations of the disclosed technology, the chelating agent may be characterized by a molarity in the range of 0.026 m to 1 m, or any sub-range thereof.

In certain implementations of the disclosed technology, the chelating agent may be selected or configured to remove metal ions from the one or more nucleic acids added to the solution.

In certain implementations of the disclosed technology, the buffering agent can include one or more of: TES (2-[[1, 3-dihydroxy-2-(hydroxymethyl)propan-2-yl]amino]ethanesulfonic acid); MOPS (3-(N-morpholino) propanesulfonic acid); PIPES (piperazine-N,N'-bis(2-ethanesulfonic acid)); MES, (2-(N-morpholino)ethanesulfonic acid); Cacodylate (dimethylarsenic acid); HEPES, (4-(2-hydroxyethyl)-1-piperazineethanesulfonic acid); tris(hydroxymethyl)aminomethane (TRIS); TAPSO (3-[N-tris(hydroxymethyl)methylamino]-2-hydroxypropanesulfonic acid); Tricine (N-[tris(hydroxymethyl)methyl]glycine); Bicine,(2-(bis(2-hydroxyethyl)amino)acetic acid); TAPS ([tris (hydroxymethyl)methylamino]propanesulfonic acid); Borate; Citric Acid; Acetic acid; KH2PO4; CHES; potassium dihydrogen phosphate, disodium hydrogen phosphate dihydrate, potassium phosphate, monobasic, anhydrous, sodium phosphate, dibasic, and/or heptahydrate.

In certain implementations of the disclosed technology, the buffering agent can include tris(hydroxymethyl)aminomethane (TRIS). In certain implementations of the disclosed technology, the buffering agent may have a molarity in the range of 0.001 m to 3 m, or any sub-range thereof.

In some implementations, the salt may be selected from among one or more of alkali metal compounds and alkaline earth metal compounds. In certain implementations of the disclosed technology, the salt may be selected from among one or more of sodium chloride, potassium chloride, magnesium sulfate, magnesium chloride, and/or calcium chloride. In certain implementations of the disclosed technology, the salt may be selected from among one or more alkali metal compounds, and/or alkaline earth metal compounds. In certain implementations of the disclosed technology, the salt may comprise NaCl. In certain implementations of the disclosed technology, the salt may be characterized by a molarity in the range of 0.15 m to 3 m, or any sub-range thereof.

In certain implementations of the disclosed technology, the salt may be selected or configured to selectively displace water to reduce degradation of the one or more nucleic acids added to the solution.

In accordance with certain exemplary implementations of the disclosed technology a solution may be configured to protect RNA and/or an RNA-based vaccine added to the solution. The solution may be configured to prevent or reduce degradation of the RNA and/or RNA-based vaccine for a duration of 1 to 180 days over a temperature range of −20 degrees C. to +38 degrees C. In certain implementations of the disclosed technology, the chelating agent can include ethylenediaminetetraacetic acid (EDTA) having a molarity in the range of 0.026 m to 1 m. In certain implementations of the disclosed technology, the buffering agent can include tris(hydroxymethyl)aminomethane (TRIS) having a molarity in the range of 0.001 m to 3 m. In certain implementations of the disclosed technology, the salt can include NaCl having a molarity in the range of 0.15 m to 3 m, or any sub-range thereof.

In accordance with certain exemplary implementations of the disclosed technology a pH of the solution is maintained in a range of 3.5 to 9. In certain implementations of the disclosed technology, the pH of the solution may be controlled by one or more of hydrochloric acid (HC), NaOH, or the buffering agent.

In certain implementations of the disclosed technology, a solution may have molar concentrations of the chelating agent, buffering agent, and salt that are characterized by initial respective molarities in the solution (or prior to being added to the mixture). In certain implementations of the disclosed technology, the solution may be diluted to simultaneously configure the final molarities of the chelating agent, buffering agent, and salt. According to certain exemplary implementations, an RNA-based vaccine may be added to the solution for storage and/or transport prior to injection. In certain implementations of the disclosed technology, the RNA can be added during processing or production to some or all of solution.

In certain implementations of the disclosed technology, an RNA-based vaccine may be added to the solution. In certain implementations of the disclosed technology, the RNA-based vaccine may be added to the solution after it has been diluted to achieve the final molarities of the chelating agent, buffering agent, and salt.

Certain implementations of the disclosed technology can include a solution and/or methods of manufacturing a solution for stabilizing and storing an RNA-based therapy suitable for dermal, subdermal, and/or intraperitoneal application in mammals. Some implementations can include preparing a solution. Certain implementations of the solution can include a chelating agent comprising ethylenediaminetetraacetic acid (EDTA); a buffering agent comprising tris(hydroxymethyl)aminomethane (TRIS); and a salt comprising NaCl. Accordingly, concentrations of the chelating agent, buffering agent, and salt may be configured for final molarities prior to addition of an RNA-based vaccine. In certain implementations of the disclosed technology, a final molarity of the chelating agent may be in the range of 0.026 m to 1 m. In certain implementations, a final molarity of the salt may be in the range of 0.15 m to 3 m. In certain implementations, a final molarity of the buffering agent may be the range of 0.001 m to 3 m. The solution may be configured to be safe for therapeutic prevention and/or treatments including but not limited to one or more of dermal, subdermal, or intraperitoneal application in mammals, or other injection applications that may be used for contact with and/or introduction into mammals. In certain implementations, the solution may be configured to protect an RNA-based vaccine and/or RNA-based therapeutic species added to the solution such that it prevents or reduces degradation of the RNA-based vaccine or RNA-based therapeutic species for a duration of 1 to 180 days over a temperature range of −20 degrees C. to +38 degrees C., or any subrange thereof.

Some implementations may enable storing and protecting the one or more nucleic acids in the solution at a temperature range from −100 degrees C. to +45 degrees C. In some implementations, the temperature range may be from about 0 degrees C. to about +40 degrees C.

Some implementations may enable storing and protecting the one or more nucleic acids in the solution at ambient temperature.

The disclosed technology may enable setting molarities of the chelating agent, the buffering agent, and the salt at concentrations and volumes that allow for injection into human tissue without toxicity. For example, in certain implementations of the disclosed technology, the chelating agent, the buffering agent, and the hypertonic salt solution components may be configured at concentrations lower than the regulatory threshold limits specified by 29 CFR 1910.1200.

Certain implementations of the disclosed technology can include a thermostable liquid solution that that allows for nucleic acids, including RNA-based vaccines, and/or extracellular RNA to be stored for extended periods and to remain substantially functional for injection into mammals.

Certain implementations of the disclosed technology can include a thermostable liquid solution that that allows for nucleic acids, including RNA species, to be stored for extended periods and to remain substantially functional for diagnostic testing.

Certain implementations may be utilized for protecting certain gene silencing therapeutics in humans and animals. The disclosed technology may be applied to therapeutics such as small interfering RNA (siRNA), antisense oligonucleotide targeting and/or aptimers.

Some implementations of the disclosed technology may utilize RNA therapy that target nucleic acids through double-stranded molecules that operate through a cellular pathway known as RNA interference (RNAi) which degrades dysfunctional or harmful proteins in the cell.

According to certain exemplary implementations, the disclosed technology may be utilized for therapeutics related to one or more of: cardiovascular disease, hepatic and Gastrointestinal disease. Neuromuscular disease, Hematologic disease, Orthopedic Disease. Integument disease, Breast disease, Endocrine Disease, Rheumatologic and Endocrine Disease, Ophthalmologic, Pulmonary, Genito-Urological, general biologic systems, related genetic diseases, and/or related acquired diseases.

The disclosed technology may provide certain advantages for use in one or more of manufacturing, logistics, transport, and/or storage.

The disclosed technology may provide certain advantages for use in one or more of cellular delivery.

Certain implementations of the disclosed technology may be utilized for vaccines and/or therapy applications that can be administered by one or more of: transdermal, intradermal, subdermal, intramuscular, intravenous, intraperitoneal, trans thecal, oral, intranasal, inhalation, trans rectal, trans urethral, trans vaginal, trans corneal, and/or application to surface of an organ or intra organ.

Certain implementation of the disclosed solutions may be used with lipid-based formulations for nucleic acid delivery including but not limited to traditional liposomes, lipoplexes, cationic nano-emulsions, and/or nanostructured lipid carriers. Certain implementation of the disclosed solutions may be used with lipid nanoparticles that may include ionizable cationic lipid, polyethelene glycol linked to lipid, phosphotidylcholines, cholesterol and natural phospholipids for vaccines, and therapeutic applications. In certain lipid nanoparticles and lipid-based formulations, targeting molecules may be added to the solution including glycomimetics or carbohydrates, and/or glycotargeting agents.

Certain implementations of the disclosed technology may be used in the treatment of viruses.

Various other uses and applications may benefit from the use of one or more of the disclosed solutions. Such uses and applications can include, but are not limited to: dynamic biologic controllers for inducible control of gene expression; gene control during transcription, post transcription, or translation; dynamic biologic controllers for high throughput detection of molecules (testing); dynamic biologic controllers for dynamic regulation of metabolic pathways; applications to screen for metabolite producing microbes and specific metabolites; use with artificial RNA; use for personalized medicine; use with precision therapy; use in therapies for enhancing wellness; and/or use in therapies that improve bone density, muscle mass, DNA repair, prevention of aging degradation, and/or improvement of cognition.

In one embodiment, the solution can be used to stabilize a variety of RNA species intracellular at ambient temperature.

In one embodiment, the solution can be used to stabilize a variety of RNA species extracellular at ambient temperature.

In one embodiment, the solution can be used to stabilize a variety of DNA species intracellular at ambient temperature.

In one embodiment, the solution can be used to stabilize a variety of DNA species extracellular at ambient temperature.

In one embodiment, the solution can be used to stabilize a variety of nucleic acids species intracellular at ambient temperature for 180 days.

In one embodiment, the solution can be used to stabilize a variety of nucleic acids species extracellular at ambient temperature for 180 days.

In one embodiment, the solution can be used to stabilize a variety of vaccines at ambient temperature.

In one embodiment, the solution can be used to stabilize a variety of RNA vaccines at ambient temperature.

In one embodiment, the solution can be used to stabilize a variety of DNA vaccines at ambient temperature.

In one embodiment, the solution can be used to store a variety of vaccines at ambient temperature.

In one embodiment, the solution can be used to store a variety of RNA vaccines at ambient temperature.

In one embodiment, the solution can be used to store variety of DNA vaccines at ambient temperature.

In one embodiment, the solution can be used to transport a variety of vaccines at ambient temperature.

In one embodiment, the solution can be used to transport a variety of RNA vaccines at ambient temperature.

In one embodiment, the solution can be used to transport variety of DNA vaccines at ambient temperature.

In one embodiment, the solution can be used to store and transport a variety of vaccines at ambient temperature.

In one embodiment, the solution can be used to store and transport a variety of RNA vaccines at ambient temperature.

In one embodiment, the solution can be used to store and transport variety of DNA vaccines at ambient temperature.

In one embodiment, the solution can be used to stabilize store and transport a variety of vaccines at ambient temperature.

In one embodiment, the solution can be used to stabilize store and transport a variety of RNA vaccines at ambient temperature.

In one embodiment, the solution can be used to stabilize store and transport variety of DNA vaccines at ambient temperature.

In one embodiment, the solution can be used to store and transport and inject and/or apply into humans and animals a variety of RNA including mRNA vaccines at ambient temperature.

In one embodiment, the solution can be used to store and transport and inject and/or apply into humans and animals a variety of DNA vaccines at ambient temperature.

In one embodiment, the solution can be used to stabilize a variety of RNA species extracellular at ambient temperature for vaccine development and application with humans and animals.

In one embodiment, the solution can be used to stabilize a variety of RNA species intracellular at ambient temperature for vaccine development and application with humans and animals.

In one embodiment, the solution can be used to stabilize a variety of DNA species extracellular at ambient temperature for vaccine development and application with humans and animals.

In one embodiment, the solution can be used to stabilize a variety of DNA species intracellular at ambient temperature for vaccine development and application with humans and animals.

Injection

According to certain exemplary embodiments, the terms "injection" or "injectable" herein may mean to transfer, incorporate, and/or introduce (or the ability thereof) into a human, mammal, and/or any other living organism by absorption, adsorption, transdermal, oral ingestion, inhalation, and injection with needles, devices, or carrying agents into human tissue, veins, arteries, muscle, fascia, bone, adipose tissue, connective tissue, neurologic tissue, fetal, stem, including transoral, intraocular, intrathecal, intrarectal, intraabdominal, intravaginal, intrauterine, intracranial, intrathoracic, or transport into the human body by other mechanisms specific to drug delivery.

In one embodiment, the solution may be used for intramuscular injection.

In one embodiment, the solution may be used for Subdermal injection.

In one embodiment, the solution may be used for intradermal injection.

In one embodiment, the solution may be used for transdermal application.

In one embodiment, the solution may be used for intramuscular injection.

In one embodiment, the solution may be used for intravenous injection.

In one embodiment, the solution may be used for intravenous IV lines, central lines injection.

In one embodiment, the solution may be used for intrathecal injection.

In one embodiment, the solution may be used for intracranial injection.

In one embodiment, the solution may be used for intraabdominal injection.

In one embodiment, the solution may be used for intraocular injection.

In one embodiment, the solution may be used for oral ingestion.

In one embodiment, the solution may be used for rectal application.

In one embodiment, the solution may be used for vaginal application.

In one embodiment, the solution may be used for uterine application.

In one embodiment, the solution may be used for gastric, or intestinal application.

In one embodiment, the solution may be used for intracystic (bladder) injection.

In one embodiment, the solution may be used with a cystoscope, endoscope or similar devices.

In one embodiment, the solution may be used with mechanical devices for insertion into human tissue.

In one embodiment, the solution may be used for injection into an organ

In one embodiment, the solution may be used for injection intracardiac

In one embodiment, the solution may be used as applied topically to an organ

Immune Response

In one embodiment, the solution may be used for applications that are intended to stimulate an immune response in humans, and or primates, and or animals.

In one embodiment, mRNA vaccines may be used as prophylactic vaccines.

In one embodiment, mRNA vaccines may be used as therapeutic vaccines.

In one embodiment, mRNA vaccines may be used as a method for gene editing.

In one embodiment, mRNA vaccines may be used as a method for cell reprogramming

In one embodiment, mRNA vaccines may be used as a method for immunotherapies

In one embodiment, mRNA vaccines may be used with induced pluripotent stem cells (iPSCs).

In accordance with certain exemplary embodiments, a solution disclosed herein can be used for delivery by Electroporation. Gene gun, Sonophoresis, Microneedles, and or naked RNA.

In accordance with certain exemplary embodiments, a solution disclosed herein can be used for delivery by Electroporation, Gene gun, Sonophoresis, Microneedles, and or naked RNA.

Lipid Constructs

In one embodiment, the solution can be used to store and transport a variety of vaccines at ambient temperature, including a variety of Lipid nano particles, (LNPs) include liposomes, lipid polycomplexes, polymer materials, micelles, polypeptides, protamine, electroporation, polymer complexes, cationic peptides or complexes, and an extensive variety of compounds that are highly efficient, non-toxic, tissue, organ, or cell-selective LNP formulations.

In one embodiment, the solution can be used to store and transport a variety of RNA vaccines at ambient temperature, including a variety of Lipid nano particles, (LNPs) include liposomes, lipid polycomplexes, polymer materials, micelles, polypeptides, protamine, electroporation, polymer complexes, cationic peptides or complexes, and an extensive variety of compounds that are highly efficient, non-toxic, tissue, organ, or cell-selective LNP formulations.

In one embodiment, the solution can be used to store and transport a variety of DNA vaccines at ambient temperature, including a variety of Lipid nano particles, (LNPs) include liposomes, lipid polycomplexes, polymer materials, micelles, polypeptides, protamine, electroporation, polymer complexes, cationic peptides or complexes, and an extensive variety of compounds that are highly efficient, non-toxic, tissue, organ, or cell-selective LNP formulations.

In one embodiment, the solution can be used to store and transport a variety of vaccines at ambient temperature, including a variety of molecules or compounds or constructs associated with mRNA, required to allow mRNA entry into cells or organs to affect protein or gene modulation, regulation, disruption, differentiation, replacement, or functional change.

In one embodiment, the solution can be used to store and transport a variety of RNA vaccines at ambient temperature, including a variety of molecules or compounds or constructs associated with mRNA, required to allow mRNA entry into cells or organs to affect protein or gene modulation, regulation, disruption, differentiation, replacement, or functional change.

In one embodiment, the solution can be used to store and transport a variety of DNA vaccines at ambient temperature, including a variety of molecules or compounds or constructs associated with mRNA, required to allow mRNA entry into cells or organs to affect protein or gene modulation, regulation, disruption, differentiation, replacement, or functional change.

In one embodiment, the solution can be used to store and transport a variety of vaccines at ambient temperature, including a variety of molecules or compounds or constructs associated with nucleic acids that act as adjuvants for functional efficacy, or as excipients.

In one embodiment, the solution can be used to store and transport a variety of vaccines at ambient temperature, including a variety of molecules or compounds or constructs associated with mRNA that act as adjuvants for functional efficacy, or as excipients.

In one embodiment, the solution can be used to store and transport a variety of vaccines at ambient temperature, including a variety of molecules or compounds or constructs associated with DNA that act as adjuvants for functional efficacy, or as excipients.

Treatments

In one embodiment, the solution can be used to store and transport a variety of vaccines at ambient temperature and apply or inject them into humans and or animals, for the treatment of infectious diseases.

In one embodiment, the solution can be used to store and transport a variety of RNA vaccines at ambient temperature and apply or inject them into humans and or animals, for the treatment of infectious diseases.

In one embodiment, the solution can be used to store and transport a variety of DNA vaccines at ambient temperature and apply or inject them into humans and or animals, for the treatment of infectious diseases.

In one embodiment, the solution can be used to store and transport a variety of vaccines at ambient temperature and apply or inject them into humans and or animals, for the treatment of fungal diseases.

In one embodiment, the solution can be used to store and transport a variety of RNA vaccines at ambient temperature and apply or inject them into humans and or animals, for the treatment of fungal diseases.

In one embodiment, the solution can be used to store and transport a variety of DNA vaccines at ambient temperature and apply or inject them into humans and or animals, for the treatment of fungal diseases.

In one embodiment, the solution can be used to store and transport a variety of vaccines at ambient temperature and apply or inject them into humans and or animals, for the treatment of diseases including tumors and cancers.

In one embodiment, the solution can be used to store and transport a variety of RNA vaccines at ambient temperature and apply or inject them into humans and or animals, for the diseases treatment of including tumors and cancers.

In one embodiment, the solution can be used to store and transport a variety of DNA vaccines at ambient temperature and apply or inject them into humans and or animals, for the diseases treatment of including tumors and cancers.

In one embodiment, the solution can be used to store and transport a variety of vaccines at ambient temperature and apply or inject them into humans and or animals, for the treatment of cardiovascular diseases.

In one embodiment, the solution can be used to store and transport a variety of RNA vaccines at ambient temperature and apply or inject them into humans and or animals, for the cardiovascular treatment of diseases.

In one embodiment, the solution can be used to store and transport a variety of DNA vaccines at ambient temperature and apply or inject them into humans and or animals, for the cardiovascular treatment of diseases.

In one embodiment, the solution can be used to store and transport a variety of vaccines at ambient temperature and apply or inject them into humans and or animals, for the treatment of neonatal diseases.

In one embodiment, the solution can be used to store and transport a variety of RNA vaccines at ambient temperature and apply or inject them into humans and or animals, for the neonatal treatment of diseases.

In one embodiment, the solution can be used to store and transport a variety of DNA vaccines at ambient temperature and apply or inject them into humans and or animals, for the neonatal treatment of diseases.

In one embodiment, the solution can be used to store and transport a variety of vaccines at ambient temperature and apply or inject them into humans and or animals, for the treatment of fetal (intrauterine) diseases.

In one embodiment, the solution can be used to store and transport a variety of RNA vaccines at ambient temperature and apply or inject them into humans and or animals, for the fetal (intrauterine) treatment of diseases.

In one embodiment, the solution can be used to store and transport a variety of DNA vaccines at ambient temperature and apply or inject them into humans and or animals, for the fetal (intrauterine) treatment of diseases.

In one embodiment, the solution can be used to store and transport a variety of vaccines at ambient temperature and apply or inject them into humans and or animals, for the treatment of genetic diseases.

In one embodiment, the solution can be used to store and transport a variety of RNA vaccines at ambient temperature and apply or inject them into humans and or animals, for the treatment of genetic diseases.

In one embodiment, the solution can be used to store and transport a variety of DNA vaccines at ambient temperature and apply or inject them into humans and or animals, for the genetic treatment of genetic diseases.

In one embodiment, the solution can be used to store and transport a variety of vaccines at ambient temperature and apply or inject them into humans and or animals, for the treatment of diabetic diseases.

In one embodiment, the solution can be used to store and transport a variety of RNA vaccines at ambient temperature and apply or inject them into humans and or animals, for the treatment of diabetic diseases.

In one embodiment, the solution can be used to store and transport a variety of DNA vaccines at ambient temperature and apply or inject them into humans and or animals, for the genetic treatment of diabetic diseases.

In one embodiment, the solution can be used to store and transport a variety of vaccines at ambient temperature and apply or inject them into humans and or animals, for the treatment of inflammatory diseases.

In one embodiment, the solution can be used to store and transport a variety of RNA vaccines at ambient temperature and apply or inject them into humans and or animals, for the treatment of inflammatory diseases.

In one embodiment, the solution can be used to store and transport a variety of DNA vaccines at ambient temperature and apply or inject them into humans and or animals, for the treatment of inflammatory diseases.

In one embodiment, the solution can be used to store and transport a variety of vaccines at ambient temperature and apply or inject them into humans and or animals, for analgesic treatments.

In one embodiment, the solution can be used to store and transport a variety of RNA vaccines at ambient temperature and apply or inject them into humans and or animals, for analgesic treatments.

In one embodiment, the solution can be used to store and transport a variety of DNA vaccines at ambient temperature and apply or inject them into humans and or animals, for analgesic treatments.

In one embodiment, the solution can be used to store and transport a variety of vaccines at ambient temperature and apply or inject them into humans and or animals, for nutritional enhancement and treatments.

In one embodiment, the solution can be used to store and transport a variety of RNA vaccines at ambient temperature and apply or inject them into humans and or animals, for nutritional enhancement and treatments.

In one embodiment, the solution can be used to store and transport a variety of DNA vaccines at ambient temperature and apply or inject them into humans and or animals, for nutritional enhancement and treatments.

In one embodiment, the solution can be used to store and transport a variety of vaccines at ambient temperature and apply or inject them into humans and or animals, for the treatment of acquired diseases.

In one embodiment, the solution can be used to store and transport a variety of RNA vaccines at ambient temperature and apply or inject them into humans and or animals, for the treatment of acquired diseases.

In one embodiment, the solution can be used to store and transport a variety of DNA vaccines at ambient temperature and apply or inject them into humans and or animals, for the treatment of acquired diseases.

In one embodiment, the solution can be used to store and transport a variety of vaccines at ambient temperature and apply or inject them into humans and or animals, for the treatment of neurologic diseases.

In one embodiment, the solution can be used to store and transport a variety of RNA vaccines at ambient temperature and apply or inject them into humans and or animals, for the treatment of neurologic diseases.

In one embodiment, the solution can be used to store and transport a variety of DNA vaccines at ambient temperature and apply or inject them into humans and or animals, for the treatment of neurologic diseases.

In one embodiment, the solution can be used to store and transport a variety of vaccines at ambient temperature and apply or inject them into humans and or animals, for the treatment of endocrine diseases.

In one embodiment, the solution can be used to store and transport a variety of RNA vaccines at ambient temperature and apply or inject them into humans and or animals, for the treatment of endocrine diseases.

In one embodiment, the solution can be used to store and transport a variety of DNA vaccines at ambient temperature and apply or inject them into humans and or animals, for the treatment of endocrine diseases.

In one embodiment, the solution can be used to store and transport a variety of vaccines at ambient temperature and apply or inject them into humans and or animals, for the treatment of hematologic diseases.

In one embodiment, the solution can be used to store and transport a variety of RNA vaccines at ambient temperature and apply or inject them into humans and or animals, for the treatment of hematologic diseases.

In one embodiment, the solution can be used to store and transport a variety of DNA vaccines at ambient temperature and apply or inject them into humans and or animals, for the treatment of hematologic diseases.

In one embodiment, the solution can be used to store and transport a variety of vaccines at ambient temperature and apply or inject them into humans and or animals, for the treatment of diseases or physiologic decline related to aging.

In one embodiment, the solution can be used to store and transport a variety of RNA vaccines at ambient temperature and apply or inject them into humans and or animals, for the treatment of diseases or physiologic decline related to aging.

In one embodiment, the solution can be used to store and transport a variety of DNA vaccines at ambient temperature and apply or inject them into humans and or animals, for the treatment of diseases or physiologic decline related to aging.

In one embodiment, the solution can be used to store and transport a variety of vaccines at ambient temperature and apply or inject them into humans and or animals, for the treatment of physiologic decline.

In one embodiment, the solution can be used to store and transport a variety of RNA vaccines at ambient temperature and apply or inject them into humans and or animals, for the treatment of physiologic decline.

In one embodiment, the solution can be used to store and transport a variety of DNA vaccines at ambient temperature and apply or inject them into humans and or animals, for the treatment of physiologic decline.

In one embodiment, the solution can be used to store and transport a variety of vaccines at ambient temperature and apply or inject them into humans and or animals, for the treatment to enhance physiologic functions.

In one embodiment, the solution can be used to store and transport a variety of RNA vaccines at ambient temperature and apply or inject them into humans and or animals, for the treatment to enhance physiologic functions.

In one embodiment, the solution can be used to store and transport a variety of DNA vaccines at ambient temperature and apply or inject them into humans and or animals, for the treatment to enhance physiologic functions.

In one embodiment, the solution can be used to store and transport a variety of vaccines at ambient temperature, and apply or inject them into humans and or animals, for nanoparticle applications for diseases treatment.

In one embodiment, the solution can be used to store and transport a variety of RNA vaccines at ambient temperature, and apply or inject them into humans and or animals, for nanoparticle applications for diseases treatment.

In one embodiment, the solution can be used to store and transport a variety of DNA vaccines at ambient temperature and apply or inject them into humans and or animals, for nanoparticle applications for diseases treatment.

In one embodiment, the solution can be used to store and transport a variety of vaccines at ambient temperature and apply or inject them into humans and or animals, for the delivery of therapeutic proteins.

In one embodiment, the solution can be used to store and transport a variety of vaccines at ambient temperature and apply or inject them into humans and or animals, for the delivery of nucleic acid drugs and therapeutics.

In one embodiment, the solution can be used to store and transport a variety of vaccines at ambient temperature and apply or inject them into humans and or animals, for medical imaging.

Certain implementations may include theranostics involving nucleic acids such as RNA and/or DNA. Theranostics can involve combining pharmaceutical and diagnostic techniques to simultaneously or sequentially diagnose and treat diseases at their earliest stages and late stages. In one embodiment, the solution can be used to store and transport a variety of vaccines at ambient temperature, and apply or inject them into humans and or animals, for medical imaging and/or theranostics.

In one embodiment, mRNA vaccines may be used for targeted gene delivery technology such as used to treat single-gene retinal degenerative diseases of RPE and prevent blindness.

In one embodiment, mRNA vaccines may be used for Fetal Delivery to multiple organs d the use of LNPs in utero to overcome the immaturity of the immune system due to the small fetal size.

In a still further alternative preferred embodiment, stabilization of RNA species may be used in applications relating to fetal development, treatment, and intrauterine delivery, and or use in pregnancy for diagnosis, modification, or treatment of fetal abnormalities, With respect to the various methods disclosed herein, in a preferred embodiment the patient or person is selected from the group consisting of a patient or person diagnosed with a condition, the condition selected from the group consisting of a disease and a disorder. In a more preferred embodiment, the condition is selected from the group consisting of acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis. Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infection; and adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus, akathesia, Alzheimer's disease, amnesia, amyotrophic lateral sclerosis (ALS), ataxias, bipolar disorder, catatonia, cerebral palsy, cerebrovascular disease Creutzfeldt-Jakob disease, dementia, depression, Down's syndrome, tardive dyskinesia, dystonias, epilepsy. Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain.

In another preferred embodiment, the condition is selected from the group consisting of cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma. X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and developmental disorders such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, for example, the brain, adrenal gland, kidney, skeletal or reproductive system.

In a still further alternative preferred embodiment, the condition is selected from the group consisting of endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In one embodiment, the solution can be used to store and transport a variety of vaccines (and constructs) at ambient temperature, and apply or inject them into humans and or animals, for cosmetics, Liposomes are also formulated in commercial products with various extracts, moisturizers, antibiotics, and proteins, for uses such as wound healing, sunburn relief, hair conditioners, antiaging products, lipsticks, hair growth stimulants, mouthwashes, skin cleansers, shampoos, antiaging, wrinkle treatment, sunscreens, and long lasting perfumes.

Non Human Treatments

In certain embodiments, a solution disclosed herein may be used in veterinarian use.

In certain embodiments, a solution disclosed herein may be used as a vaccine in veterinarian use.

In certain embodiments, a solution disclosed herein may be used as a RNA vaccine in veterinarian use.

In certain embodiments, a solution disclosed herein may be used as a DNA vaccine in veterinarian use.

In certain embodiments, a solution disclosed herein may be used as a vaccine in veterinarian use for Equine, Feline, Canine, Rabbit, Farm animal, including Goats, Sheep, Pigs, Cattle, Zebu, Donkeys, Water buffaloes, Dromedary camel, Horse, Yak, Domestic Bactrian camel, Llama, Alpaca, Gayal, Bali cattle, Domestic rabbit, Addax, Bison, Deer, Eland, Elk, Guinea pig, Greater kudu, Mule, Moose, Muskox, Reindeer, birds, Chicken, Domestic duck, Domestic goose, Domestic guinea fowl, Domestic Muscovy duck, Domestic turkey, Emu, Egyptian goose, Indian peafowl, Mute swan, Ostrich, Partridge, Small-billed tinamou, Pigeon, Quail, Edible-nest swiftlet, Grey francolin, Guineafowl, Common pheasant, and/or Golden pheasant.

In certain embodiments, a solution disclosed herein may be used as a vaccine component in amphibians, mammals, birds, fishes, reptiles, invertebrates, insects, and/or any other living organisms.

In one embodiment, the solution can be used to store and transport a variety of vaccines at ambient temperature, and apply or inject them into humans and or animals, for the agriculture applications for diseases and optimization of production.

In one embodiment, the solution can be used to store and transport a variety of RNA vaccines at ambient temperature, and apply or inject them into humans and or animals, for the agriculture applications for diseases and optimization of production.

In one embodiment, the solution can be used to store and transport a variety of DNA vaccines at ambient temperature, and apply or inject them into humans and or animals, for the agriculture applications for diseases and optimization of production.

In one embodiment, the solution can be used to store and transport a variety of vaccines at ambient temperature, and apply or inject them into humans and or animals, for the agriculture applications for diseases and optimization of production.

Solution

Stabilization of extracellular RNA including mRNA and tRNA, and rRNA, RNAi, siRNA, in a solution at ambient temperature. The solution may include a chelating agent, such as EDTA, (ethylenediaminetetraacetic acid). The EDTA may bind to metal ions. In certain implementations, a Sodium Chloride hypertonic solution may be added in part to stabilize the RNA, for example, by allowing for Na+ to selectively displace water-reducing degradation of the RNA components. In certain implementations, Tris (tris(hydroxymethyl) aminomethane) may be added to maintain the pH of the solution for RNA stabilization. According to certain exemplary implementations of the disclosed technology, the EDTA, hypertonic NaCl, and Tris may be combined in a concentration that is reliable and effective in stabilizing RNA, which is neither obvious nor trivial.

EDTA may bind divalent cations such as calcium and magnesium at a range of concentrations from about 0.3 Molar to about 1.25 Molar. In certain implementations, EDTA can contribute to neutralizing Mg++ required for some polymerase activity. According to certain implementations, EDTA alone may not be found to be effective in eliminating the effect of RNase on RNA.

Sodium Chloride hypertonic solution may be added as noted in part to stabilize the RNA by allowing for Na+ to selectively displace water-reducing degradation of the RNA components. Sodium may function at these concentrations to inhibit the effects of RNase.

Ranges

Tris (tris(hydroxymethyl) aminomethane) may be added to maintain the pH of the solution for RNA stabilization with a pKa of 8.1, being an effective buffer between pH of 7 and 9, and in the range of 3.5 to 11.

As discussed herein the term "crenation" describes a process of cellular water loss through osmosis. Cells are usually in an isotonic solution inside the body, meaning that there is the same concentration of solute and water both inside and outside the cells. This equilibrium allows the cells to keep their shape, with water moving in and out at a constant rate and maintaining the same osmotic pressure across the semipermeable membrane. However, when this equilibrium is disrupted by the presence of a higher concentration of solute in the solution, it creates a hypertonic environment, which causes the intracellular water to diffuse out, which may cause the cells to shrivel.

In accordance with certain exemplary embodiments of the disclosed technology, a high concentration of NaCl may not only causes cell crenation and membrane disruption but may also stop Type II nuclease activity completely and may further facilitate the dissociation of proteins. In certain implementations of the disclosed embodiments, a combination of EDTA with a high NaCl concentration may virtually stop all nuclease activity. In certain implementations, the Tris buffer may stabilize and maintain the pH of the solution, preventing degradation of the RNA at acid pH, and/or preventing the precipitation of EDTA and NaCl at ranges of pH 3.5-11.

The pH of the compound has a direct effect on the solubility, bioavailability, and functionality of the injected or applied active or passive components noted. The pH ranges can be modified for the specific component, for functionality, and to minimize pain, discomfort, and or potential tissue damage or physiologic disruption at the application site.

In one embodiment, stabilization of intracellular and or extracellular RNA including tRNA (transfer RNA), mRNA (messenger RNA), and rRNA (Ribosomal RNA), RNAi (RNA Interference), siRNA (small interfering RNA) snRNA, snoRNA, siRNA tmRNA, dsRNA may be achieved in a solution at ambient temperature with the ability to store at lower temperatures for convenience or specialized applications.

Example Embodiment: Stabilization of Intracellular RNA at Ambient Temperature For Injection—Stabilization of intracellular RNA which may include mRNA and tRNA, and rRNA snRNA snoRNA siRNA tmRNA dsRNA RNAi in a solution may be stabilized with agents that are in concentrations and volumes that allow for injection into human tissue without toxicity at ambient temperature.

Example Embodiment: Stabilization of Extracellular RNA at Ambient Temperature For Injection—Stabilization of extracellular RNA which may include mRNA and tRNA, and rRNA snRNA snoRNA siRNA tmRNA dsRNA RNAi in a solution with agents that are in concentrations and volumes that allow for injection into human tissue without toxicity at ambient temperature.

Example Embodiment; Stabilization of Intracellular DNA at Ambient Temperature For Injection—Stabilization of intracellular DNA in a solution may be stabilized with agents that are in concentrations and volumes that allow for injection into human tissue without toxicity at ambient temperature.

Example Embodiment: Stabilization of Extracellular DNA at Ambient Temperature For Injection—Stabilization of extracellular DNA in a solution with agents that are in concentrations and volumes that allow for injection into human tissue without toxicity at ambient temperature.

Example Embodiment: Stabilization of Intracellular RNA For Injection at Ambient Temperature and Variable Temperature w/out Membrane Lysis. Stabilization of intracellular RNA which may include mRNA and tRNA, and rRNA snRNA snoRNA siRNA tmRNA dsRNA RNAi in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Extracellular RNA For Injection at Ambient Temperature and Variable Temperature w/out Membrane Lysis. Stabilization of extracellular RNA which may include mRNA and tRNA, and rRNA snRNA snoRNA siRNA tmRNA dsRNA RNAi in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Intracellular DNA For Injection at Ambient Temperature and Variable Temperature w/out Membrane Lysis. Stabilization of intracellular DNA in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Extracellular DNA For Injection at Ambient Temperature and Variable Temperature w/out Membrane Lysis. Stabilization of extracellular DNA in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Intracellular RNA For Injection at Ambient Temperature and Variable Temperature with Membrane Lysis. Stabilization of intracellular RNA which may include mRNA and tRNA, and rRNA snRNA snoRNA siRNA tmRNA dsRNA RNAi in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Extracellular RNA For Injection at Ambient Temperature and Variable Temperature with Membrane Lysis. Stabilization of extracellular RNA which may include mRNA and tRNA, and rRNA snRNA snoRNA siRNA tmRNA dsRNA RNAi in a solution at ambient temperature and variable temperatures. The combination and concentrations of the NaCl, EDTA, and Tris allow for crenation of the cell that can occur without cell membrane lysis and does not require mechanical dehydration, freeze-drying, use of ETOH, or other compounds that would not be appropriate for injection into human tissue.

Example Embodiment: Stabilization of Intracellular/Extracellular DNA with Membrane Lysis Stabilization of DNA in a solution at ambient temperature and variable temperatures. The combination and concentrations of the NaCl, EDTA, and Tris allow for crenation of the cell that can occur with cell membrane lysis and does not require mechanical dehydration, freeze-drying, use of ETOH, or other compounds that would not be appropriate for injection into human tissue.

Example Embodiment: Stabilization of Intracellular/Extracellular DNA without Membrane Lysis Stabilization of DNA segments in a solution at ambient temperature and variable temperatures. The combination and concentrations of the NaCl, EDTA, and Tris allow for crenation of the cell that can occur with cell membrane lysis and does not require mechanical dehydration, freeze-drying, use of ETOH, or other compounds that would not be appropriate for injection into human tissue.

Example Embodiment: Stabilization of Intracellular/Extracellular Proteins For Injection at Ambient temperature and variable temperatures with or without Membrane Lysis—. Stabilization of protein Segments in a solution at ambient temperature and variable temperatures. The combination and concentrations of the NaCl, EDTA, and Tris allow for crenation of the cell that can occur with cell membrane lysis and does not require mechanical dehydration, freeze-drying, use of ETOH, or other compounds that would not be appropriate for injection into human tissue.

Example Embodiment: Stabilization of Intracellular/Extracellular Vaccine components. For Injection Ambient temperature and variable temperatures. Stabilization of Vaccine components including protein, genetic material (DNA, RNA, and derivatives) in a solution at ambient temperature and variable temperatures. The combination and concentrations of the 6 and 5 and do not require mechanical dehydration, freeze-drying, use of ETOH, or other compounds that would not be appropriate for injection into human tissue.

Example Embodiment: Stabilization of plasmids, and genetic components, fragments of genetic components, consisting of RNA, RNA segments, RNA components, and nucleic acids used for purposes of vaccination, eliciting an immune response.

In one embodiment, the solution may be used to stabilize nucleic acids at an ambient temperature allowing for an extensive variety of downstream applications.

In one embodiment, the solution may be used to stabilize nucleic acids at ambient temperature without denaturing effects on the nucleic acids allowing for an extensive variety of downstream applications.

Example Formulation of a Solution

In accordance with an exemplary embodiment of the disclosed technology, the following components techniques used to produce a solution for stabilizing RNA and/or other nucleic acids:
- Sodium Chloride (NaCL) Molar 29.22 gm/m (with range of 0.15 m to 3.0 m);
- Ethylenediamine tetraacetic acid (EDTA) 292.24 gm/m (with range of 0.026 m to 1.0 m);
- Tris (tris(hydroxymethyl) aminomethane) (Tris) 121.14 gm/m. (with range of 0.001 m to 3.0 m);
- Double distilled sterile RNAse/DNAse free $H_2O$ used to finalize volume to 1.0 liters;
- Adjust pH of final volume to 7.0, 7.1 . . . to 8.1, 8.2, 8.3, 8.4, and 8.5 with concentrated HCL (and or other acids), or NaOH (with a range of pH3.5-pH11);
- Strain through 0.22 Micron filter.

Using the above example formulation of the solution, RNA was stable in solution at room temp for 12 days and 60 days at 38 degrees C. with minimal cycle increase indicating stability without degradation using Real-Time Quantitative PCR on ThermoFisher QuantStudio 12K FLEX. Three SARS-CoV-2 P patient sample in Viral Transport Media were spiked with BEI resources Genomic RNA from SARS related Coronavirus 2 (Cat #NR52285) to have final concentrations of 10000, 1000 and 100 copies per ml after adding 100 ul to 50%, 75% and 100% concentrated Stabilization solution. Samples were then extracted and run using the Thermofisher Taqpath COV ID-19 kit. TABLE 1 below summarizes the results of the initial PCR test after one day.

TABLE 1

| Sample Name | Internal Control Ct | COVID-19 Target | Covid 19 target Ct | Copies per MI |
|---|---|---|---|---|
| 2473 - 50E | 27.2 | N Protein | 26.2 | 10000 |
| 2473 - 75E | 27.2 | N Protein | 26.3 | 10000 |
| 2473 - NS | 28.2 | N Protein | 27.2 | 10000 |
| 2831 - 50E | 28.0 | N Protein | 0.0 | 1000 |
| 2831 - 75E | 27.6 | N Protein | 34.4 | 1000 |
| 2831 - NS | 28.3 | N Protein | 0.0 | 1000 |
| 3690 - 50E | 27.3 | N Protein | 32.4 | 100 |
| 3690 - 75E | 27.7 | N Protein | 32.3 | 100 |
| 3690 - NS | 28.9 | N Protein | 32.1 | 100 |

Samples were then kept at ambient temperature for 10 days and retested. TABLE 2 below shows the PCR test results after 10 days.

TABLE 2

| Sample Name | Internal Control Ct | COVID-19 Target | Covid 19 target Ct | Copies per MI |
|---|---|---|---|---|
| 2473-50E | 27.8 | N Protein | 28.2 | 10000 |
| 2473--75E | 28.1 | N Protein | 27.4 | 10000 |
| 2473NS | 29.5 | N Protein | 28.3 | 10000 |
| 2831-50E | 29.0 | N Protein | 0.0 | 1000 |
| 2831-75E | 28.9 | N Protein | 0.0 | 1000 |
| 2831-NS | 29.5 | N Protein | 36.6 | 1000 |
| 3690-50E | 28.7 | N Protein | 33.8 | 100 |
| 3690--5E | 28.7 | N Protein | 33.7 | 100 |
| 3690-NS | 30.6 | N Protein | 36.3 | 100 |

In certain implementations, stabilization of extracellular RNA including mRNA and tRNA, and rRNA may be achieved in a solution with agents that are in concentrations and volumes that allow for injection into human tissue without toxicity at ambient temperature. e.g., 15 to 38° C. (59 to 100.4° F.). TABLE 3 below lists example temperature stabilization ranges, according to certain exemplary embodiments of the disclosed technology. Any of the ranges listed in TABLE 3 may be combined with adjacent ranges or groups of ranges to form temperature ranges over which the disclosed solution may stabilize the RNA to prevent or reduce degradation.

TABLE 3

| Temperature stabilization ranges |
|---|
| −90 C. to −81 C. |
| −80 C. to −71 C. |
| −70 C. to −61 C. |
| −60 C. to −51 C. |
| −50 C. to −41 C. |
| −40 C. to −31 C. |
| −30 C. to −21 C. |
| −20 C. to −11 C. |
| −10 to 0 C. |
| 0 to 9 C. |
| 10-20 C. |
| 21 to 29 C. |
| 30 to 35 C. |
| 36 to 40 C. |
| 41 to 50 C. |
| 51 to 60 C. |

In accordance with certain exemplary implementations of the disclosed technology ambient temperature may be defined herein as ranging between −20 C (−4 F) to 38 C (100.4 F). Ambient temperature, as defined herein, can include temperatures common in both shipping and storage, and not just room temperature.

Buffers

In certain exemplary implementations, a buffer solution may be added to adjust and/or maintain the pH of stabilizing solution for RNA stabilization. According to certain implementation, one or more buffer solutions may be added to the mixture of components in the stabilizing solution to stabilize the pH in various ranges from about 3.5-3.6 to about 10.9-11.0.

In certain exemplary implementations, the solution can be used to stabilize lipid nanoparticles which contain an ionizable lipid which is positively charged at low pH (enabling RNA complexation) and neutral at physiological pH (reducing the potential toxic effects and facilitating payload release).

TABLE 4 below lists examples of resulting-pH values and ranges of the stabilizing solution, according to certain exemplary embodiments. According to certain implementations of the disclosed technology, any of the pH ranges listed in TABLE 4 may be combined with adjacent ranges or groups of ranges to form pH ranges over which the disclosed solution may be prepared for stabilizing the RNA to prevent or reduce degradation.

TABLE 4

| pH Ranges |
| --- |
| 3.5-3.6 |
| 3.6-3.7 |
| 3.7-3.8 |
| 3.8-3.9 |
| 3.9-4.0 |
| 4.0-4.1 |
| 4.1-4.2 |
| 4.2-4.3 |
| 4.3-4.4 |
| 4.4-4.5 |
| 4.5-4.6 |
| 4.6-4.7 |
| 4.7-4.8 |
| 4.8-4.9 |
| 4.9-5.0 |
| 5.0-5.1 |
| 5.1-5.2 |
| 5.2-5.3 |
| 5.3-5.4 |
| 5.4-5.5 |
| 5.5-5.6 |
| 5.6-5.7 |
| 5.7-5.8 |
| 5.8-5.9 |
| 5.9-6.0 |
| 6.0-6.1 |
| 6.1-6.2 |
| 6.2-6.3 |
| 6.3-6.4 |
| 6.4-6.5 |
| 6.5-6.6 |
| 6.6-6.7 |
| 6.7-6.8 |
| 6.8-6.9 |
| 6.9-7.0 |
| 7.0-7.1 |
| 7.1-7.2 |
| 7.2-7.3 |
| 7.3-7.4 |

TABLE 4-continued

| pH Ranges |
| --- |
| 7.4-7.5 |
| 7.5-7.6 |
| 7.6-7.7 |
| 7.7-7.8 |
| 7.8-7.9 |
| 7.9-8.0 |
| 8.0-8.1 |
| 8.1-8.2 |
| 8.2-8.3 |
| 8.3-8.4 |
| 8.4-8.5 |
| 8.5-8.6 |
| 8.6-8.7 |
| 8.7-8.8 |
| 8.8-8.9 |
| 8.9-9.0 |
| 9.0-9.1 |
| 9.1-9.2 |
| 9.2-9.3 |
| 9.3-9.4 |
| 9.4-9.5 |
| 9.5-9.6 |
| 9.6-9.7 |
| 9.7-9.8 |
| 9.8-9.9 |
| 9.9-10.0 |
| 10.0-10.1 |
| 10.1-10.2 |
| 10.2-10.3 |
| 10.3-10.4 |
| 10.4-10.5 |
| 10.5-10.6 |
| 10.6-10.7 |
| 10.7-10.8 |
| 10.8-10.9 |
| 10.9-11.0 |

In one embodiment, the salt concentrations used can be made to be supersaturated and combined with the chelating agent and buffering agent in the ranges described (to allow for stabilization of nucleic acids).

In the embodiment described above, the resulting solution may require dilution with water or other hypotonic agents to allow for injectability into human and or animal tissue.

In the embodiment described above, additional adjustments in buffer and chelating agent may be performed to maintain final concentration to provide stability of RNA and RNA constructs including vaccines.

Additional Buffers

In accordance with certain exemplary embodiments, a solution disclosed herein can be used to stabilize one or more of the following constituents that can be used as vehicles for delivery of vaccines, and a variety of therapeutics: potassium dihydrogen phosphate, disodium hydrogen phosphate dihydrate, potassium phosphate monobasic anhydrous, sodium phosphate dibasic heptahydrate, potassium dihydrogen phosphate, and/or disodium hydrogen phosphate dihydrate.

Osmolarity

In one embodiment, the osmolarity can range from 300 milliosmoles to 600 for intramuscular injection and 300-1000 for large vein or central line injection (up to 1250 milliosmoles).

In one embodiment, the osmolarity can range from 350 milliosmoles to 400 milliosmoles for injection and or insertion into human tissue.

In one embodiment, the osmolarity can range from 400 milliosmoles to 450 milliosmoles for injection and or insertion into human tissue.

In one embodiment, the osmolarity can range from 450 milliosmoles to 500 milliosmoles for injection and or insertion into human tissue.

In one embodiment, the osmolarity can range from 500 milliosmoles to 550 milliosmoles for injection and or insertion into human tissue.

In one embodiment, the osmolarity can range from 550 milliosmoles to 600 milliosmoles for injection and or insertion into human tissue.

In one embodiment, the osmolarity can range from 600 milliosmoles to 650 milliosmoles for injection and or insertion into human tissue.

In one embodiment, the osmolarity can range from 650 milliosmoles to 700 milliosmoles for injection and or insertion into human tissue.

In one embodiment, the osmolarity can range from 700 milliosmoles to 750 milliosmoles for injection and or insertion into human tissue.

In one embodiment, the osmolarity can range from 750 milliosmoles to 800 milliosmoles for injection and or insertion into human tissue.

In one embodiment, the osmolarity can range from 800 milliosmoles to 850 milliosmoles for injection and or insertion into human tissue.

In one embodiment, the osmolarity can range from 850 milliosmoles to 900 milliosmoles for injection and or insertion into human tissue.

In one embodiment, the osmolarity can range from 900 milliosmoles to 1000 milliosmoles for injection and or insertion into human tissue.

In one embodiment, the osmolarity can range from 1000 milliosmoles to 1050 milliosmoles for injection and or insertion into human tissue.

In one embodiment, the osmolarity can range from 1050 milliosmoles to 1100 milliosmoles for injection and or insertion into human tissue.

In one embodiment, the osmolarity can range from 1100 milliosmoles to 1150 milliosmoles for injection and or insertion into human tissue.

In one embodiment, the osmolarity can range from 1150 milliosmoles to 1200 milliosmoles for injection and or insertion into human tissue.

In one embodiment, the osmolarity can range from 1200 milliosmoles to 2500 milliosmoles for injection and or insertion into human tissue after treatments to reduce osmolarity compatibility with living tissue.

Lipids LNP

In accordance with certain exemplary embodiments, a solution disclosed herein can be used to stabilize one or more of the following constituents that can be used in liposome, LNPs, and other vehicles including solid lipid nanoparticles, and nanostructured lipid carriers:
Phospholipids
Phosphatidylcholines
Phosphatidylserines
Phosphatidylglycerols In accordance with certain exemplary embodiments, a solution disclosed herein can be used to stabilize one or more of the following constituents that can be used as vehicles for delivery of vaccines, and a variety of therapeutics:
liposome, LNPs, and including solid lipid nanoparticles, and nanostructured lipid carriers, cationic lipid nanoparticles, non-lamellar lipid nanoparticles, cubosomes, hexasomes, micelles, reverse micelles, ethosomes, echogenic liposomes, multilaminar LNPs, and LNP modifications such as targeted liposomes, stealth liposomes (liposomes coated with a variety of biocompatible inert polymers, such as poly-(ethylene glycol) (PEG) increasing efficacy including reducing phagocytes, Stimuli-Responsive Liposomes (Liposomes responsive to temperature, changes in pH, enzymes, light, magnetic and electrical fields, and ultrasound).

In accordance with certain exemplary embodiments, a solution disclosed herein can be used to stabilize one or more of the following constituents that can be used in liposome, LNPs, and other vehicles including solid lipid nanoparticles, and nanostructured lipid carriers:
Triglycerides
   Trimyristin (Dynasan 114)
   Tristearin (Dynasan 118)
Mono-, Di-, and Triglyceride Mixtures
   Witeposol bases
   Glyceryl stearates (Imwitor 900)
   Glyceryl behenates (Compritol 888 ATO)
   Glyceryl palmitostearates (Precirol ATO 5)
Waxes
   Beeswax
   Cetyl palmitate
Hard Fats
   Stearic acid Sodium oleate
   Palmitic acid
   Behenic acid
Other Lipids
   Miglyol 812
   Paraffin In accordance with certain exemplary embodiments, a solution disclosed herein can be used to stabilize one or more of the following constituents that can be used in liposome, LNPs, and other vehicles including solid lipid nanoparticles, and nanostructured lipid carriers:
Emulsifiers/Co-Emulsifiers
   Lecithin
   Poloxamer 188
   Poloxamer 407
   Tyloxapol
   Polysorbate 20
   Polysorbate 60
   Polysorbate 80
   Sodium cholateSodium glycocholate
   Taurodeoxycholic acid sodium
   Butanol and Butyric acid
   Cetylpyridinium chloride
   Sodium dodecyl sulfate
   Sodium oleate
   Polyvinyl alcohol
   Cremophor EL In accordance with certain exemplary embodiments, a solution disclosed herein can be used to stabilize one or more of the following:
   LNP, lipid nanoparticles (ionizable cationic lipid);
   PEG, cholesterol, phospholipids);
   Phospholipids
   Phosphatidylcholines
   Phosphatidylserines
   Phosphatidylglycerols
   PEG, polyethylene glycol;
   DOTAP, dioleoyl-3-trimethylammonium propane;
   DOPE, dioleoylphosphatidylethanolamine;

DC-Cholesterol, 3_-[N—(N',N'-dimethylaminoethane) carbamoyl];
DOTMA, N-[1-(2,3-dioleoyloxy)propyl]-N,N,Ntrimethylammonium chloride;
PBAE, poly(_-amino ester); PSA, polyethyleneimine-stearic acid;
PEI, polyethylenimine;
DEAE, diethylaminoethyl;
hPBAEs, hyperbranched poly(beta amino esters);
PEG[Glu(DET)]2, N-substituted polyethylene glycol-di-block-polyglutamide;
PLGA, poly(lactic-co-glycolic acid);
CLAN, cationic lipid-assisted nanoparticles;
BHEM-cholesterol;
N-bis(2-hydroxyethyl)-N-methyl-N-(2-cholesteryloxy-carbonyl aminoethyl) ammonium bromide.

In accordance with certain exemplary embodiments, a solution disclosed herein can be used to stabilize nucleic acids encapsulated in, and/or associated with:
LNP, lipid nanoparticles (ionizable cationic lipid);
PEG, cholesterol, phospholipids);
PEG, polyethylene glycol;
DOTAP, dioleoyl-3-trimethylammonium propane;
DOPE, dioleoylphosphatidylethanolamine;
DC-Cholesterol, 3_-[N—(N',N'-dimethylaminoethane) carbamoyl];
DOTMA, N-[1-(2,3-dioleoyloxy)propyl]-N,N,Ntrimethylammonium chloride;
PBAE, poly(_-amino ester); PSA, polyethyleneimine-stearic acid;
PEI, polyethylenimine;
DEAE, diethylaminoethyl;
hPBAEs, hyperbranched poly(beta amino esters);
PEG[Glu(DET)]2, N-substituted polyethylene glycol-di-block-polyglutamide;
PLGA, poly(lactic-co-glycolic acid);
CLAN, cationic lipid-assisted nanoparticles;
BHEM-cholesterol;
N-bis(2-hydroxyethyl)-N-methyl-N-(2-cholesteryloxy-carbonyl aminoethyl) ammonium bromide.
DSPC distearoylphosphatidylcholine
1,2-Distearoyl-sn-glycero-3-phosphocholine (DSPC)
DLin-MC3-DMA: (6Z,9Z,28Z,31Z)-heptatriaconta-6,9,28,31-tetraen-19-yl-4-(dimethylamino) butanoate
PEG2000-DMG=Alpha-(3'-{[1,2-di(myristoyloxy)propanoxy] carbonylamino}propyl)-ω-methoxy, polyoxyethylene
ALC-0315=(4-hydroxybutyl) azanediyl)bis (hexane-6,1-diyl)bis(2-hexyldecanoate)
ALC-0159=2-[(polyethylene glycol)-2000]-N,N ditetradecylacetamide
SM-102 (heptadecan-9-yl 8-((2-hydroxyethyl) (6-oxo-6-(undecyloxy) hexyl) amino) octanoate} PEG2000-DMG=1-monomethoxypolyethyleneglycol-2,3-dimyristylglycerol with polyethylene glycol.

In one embodiment, a solution disclosed herein may be used to stabilize nanoparticles comprised of lipids.

In one embodiment, a solution disclosed herein may be used to stabilize lipids.

In one embodiment, a solution disclosed herein may be used in applications for plasmids In one embodiment, a solution disclosed herein may be used to replace stabilizing agents for vaccines that rely on genetic material for application.

In one embodiment, a solution disclosed herein may be used to augment stabilizing agents for vaccines that rely on genetic material for application.

In one embodiment, a solution disclosed herein may be used as a stabilizing agents for vaccines that rely on genetic material for application.

In one embodiment, initial storage of a solution disclosed herein may be used as-is and/or diluted based on application. Temperature In one embodiment a diluted product (wherein the "product" may be a solution disclosed herein) can be maintained at ambient temperature for 1 day.

In one embodiment, a diluted product can be maintained at ambient temperature for 2 days.

In one embodiment, a diluted product can be maintained at ambient temperature for 3 days.

In one embodiment, a diluted product can be maintained at ambient temperature for 4 days.

In one embodiment, a diluted product can be maintained at ambient temperature for 5 days.

In one embodiment, a diluted product can be maintained at ambient temperature for 6 days.

In one embodiment, a diluted product can be maintained at ambient temperature for 7 days.

In one embodiment, a diluted product can be maintained at ambient temperature for 8 days.

In one embodiment, a diluted product can be maintained at ambient temperature for 9 days.

In one embodiment, a diluted product can be maintained at ambient temperature for 10 days.

In one embodiment, a diluted product can be maintained at ambient temperature for 11 days.

In one embodiment, a diluted product can be maintained at ambient temperature for 12 days.

In one embodiment, a diluted product can be maintained at ambient temperature for 13 days.

In one embodiment, a diluted product can be maintained at ambient temperature for 14 days.

In one embodiment, a diluted product can be maintained at ambient temperature for 14-21 days.

In one embodiment, a diluted product can be maintained at ambient temperature for 21-28 days.

In one embodiment, a diluted product can be maintained at ambient temperature for 1-3 months.

In one embodiment, a diluted product can be maintained at ambient temperature for 3-6 months.

In one embodiment, a diluted product can be maintained at ambient temperature for 6-9 months.

In one embodiment, a diluted product can be maintained at ambient temperature for 9-12 months.

In one embodiment, a diluted product can be maintained at ambient temperature for 1-2 years.

In one embodiment, a diluted product can be maintained at ambient temperature for 2-3 years.

In one embodiment, a diluted product can be maintained at ambient temperature for 3-4 years.

In one embodiment, a diluted product can be maintained at ambient temperature for 4-5 years.

In one embodiment, a diluted product can be maintained at ambient temperature for 5-6 years.

In one embodiment, a diluted product can be maintained at ambient temperature for 6-7 years.

In one embodiment, a diluted product can be maintained at ambient temperature for 7-8 years.

In one embodiment, a diluted product can be maintained at ambient temperature for 8-9 years.

In one embodiment, a diluted product can be maintained at ambient temperature for 9-10 years.

In one embodiment, a diluted product can be maintained at ambient temperature for 10-15 years.

In one embodiment, a diluted product can be maintained at ambient temperature for 15-21 years.

In one embodiment, a diluted product can be maintained at 24 to 45 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at 0 to 24 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at 0 to −2 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −8 to −2 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −20 to −8 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −30 to −40 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −640 to −40 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −80 to −60 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

In one embodiment, a diluted product can be maintained at −100 to −80 degree C. for 1 day, 2 days, 3 days, 4 days, 5 days, 6 days, 7 days, 8 days, 9 days, 10 days, 11 days, 12 days, 13 days 14 days, 15-21 days, 21-28 days, 1-3 months, 3-6 months, 6-9 months, 9-12 months, 1-2 years, 2-3 years, 3-4 years, 4-5 years, 5-6 years, 6-7 years, 7-8 years, 8-9 years, 9-10 years, 10-15 years, 15-21 years.

Throughout the specification and the claims, the following terms take at least the meanings explicitly associated herein, unless the context clearly dictates otherwise. Relational terms such as "first" and "second," and the like may be used solely to distinguish one entity or action from another entity or action without necessarily requiring or implying any actual such relationship or order between such entities or actions. The term "or" is intended to mean an inclusive "or." Further, the terms "a," "an," and "the" are intended to mean one or more unless specified otherwise or clear from the context to be directed to a singular form. The term "include" and its various forms are intended to mean including but not limited to.

In the previous description, numerous specific details are set forth. However, it is to be understood that embodiments of the disclosed technology may be practiced without these specific details. References to "one embodiment," "an embodiment," "example embodiment," "various embodiments," and other like terms indicate that the embodiments of the disclosed technology so described may include a particular function, feature, structure, or characteristic, but not every embodiment necessarily includes the particular function, feature, structure, or characteristic. Further, repeated use of the phrase "in one embodiment" does not necessarily refer to the same embodiment, although it may.

It is important to recognize that it is impractical to describe every conceivable combination of components or methodologies for purposes of describing the claimed subject matter. However, a person having ordinary skill in the art will recognize that many further combinations and permutations of the subject innovations are possible. Accordingly, the claimed subject matter is intended to cover all such alterations, modifications and variations that are within the spirit and scope of the claimed subject matter.

Although the present disclosure describes specific examples, embodiments, and the like, various modifications and changes may be made without departing from the scope of the present disclosure as set forth in the claims below. For example, although the example methods, devices, systems, or articles of manufacture described herein are in conjunction with remote device configuration, the skilled artisan will readily recognize that the example methods, devices, systems, or articles of manufacture may be used in other methods, devices, systems, or articles of manufacture and may be configured to correspond to such other example methods, devices, systems, or articles of manufacture as needed. Further, while at least one example, embodiment, or the like has been presented in the foregoing detailed description, many variations exist. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all of the claims. Any benefits, advantages, or solutions to problems that are described herein with regard to specific examples, embodiments, or the like are not intended to be construed as a critical, required, or essential feature or element of any or all of the claims.

We claim:

1. A solution for stabilizing an injectable RNA-based vaccine having a lipid-based carrier, the solution consisting essentially of:
   ethylenediaminetetraacetic acid (EDTA) having a molarity in the range of 0.026M to 1M;
   tris(hydroxymethyl)aminomethane (TRIS) having a molarity in the range of 0.06M to 0.6M; and
   a salt;

wherein the solution protects against degradation of the injectable RNA-based vaccine having a lipid based carrier added to the solution in a temperature range of +10 degrees C. to +45 degrees C. for a duration of 3 days to 40 days; and wherein the solution is safe for injection into mammals.

2. The solution of claim 1, wherein the salt is selected from the group consisting of sodium chloride, potassium chloride, magnesium sulfate, magnesium chloride, calcium chloride, and combinations thereof.

3. The solution of claim 1, wherein the salt is hypertonic in solution, and wherein the salt is selected from the group consisting of sodium chloride, potassium chloride, magnesium sulfate, magnesium chloride, calcium chloride, alkali metal salts alkaline earth metal salts, and combinations thereof.

4. The solution of claim 1, wherein the salt is hypertonic in solution, and wherein the hypertonic salt is NaCl having a molarity in the range of 0.15M to 3M.

5. The solution of claim 1, wherein a pH of the solution is in a range of 7.1 to 9.0.

6. The solution of claim 5, wherein the pH of the solution has been controlled by addition of one or more of hydrochloric acid (HCl), NaOH, or the TRIS.

7. A solution for stabilizing nucleic acids, the solution consisting essentially of:
ethylenediaminetetraacetic acid (EDTA) having a molarity in the range of 0.026M to 1M;
tris(hydroxymethyl)aminomethane (TRIS) having a molarity in the range of 0.06M to 0.6M; and
a salt;
wherein the solution protects against degradation of RNA added to the solution in a temperature range of +10 degrees C. to +45 degrees C. for a duration of 3 days to 40 days.

8. The solution of claim 7, wherein the salt is selected from the group consisting of sodium chloride, potassium chloride, magnesium sulfate, magnesium chloride, calcium chloride, and combinations thereof.

9. The solution of claim 7, wherein the salt is hypertonic in solution, and wherein the salt is selected from the group consisting of sodium chloride, potassium chloride, magnesium sulfate, magnesium chloride, calcium chloride, alkali metal salts, alkaline earth metal salts, and combinations thereof.

10. The solution of claim 7, wherein the salt is NaCl having a molarity in the range of 0.15M to 3M.

11. The solution of claim 7, wherein a pH of the solution is in a range of 7.1 to 9.0.

12. The solution of claim 11, wherein the pH of the solution has been controlled by addition of one or more of hydrochloric acid (HCl), NaOH, or the TRIS.

13. A method of manufacturing a solution for stabilizing and storing an injectable RNA-based vaccine having a lipid-based carrier, the method comprising:
preparing a solution, the solution comprising:
a chelating agent comprising ethylenediaminetetraacetic acid (EDTA);
a buffering agent comprising tris(hydroxymethyl)aminomethane (TRIS); and
a salt comprising NaCl;
configuring concentrations of the chelating agent, buffering agent, and salt for final molarities prior to addition of an RNA-based vaccine, wherein:
a final molarity of the chelating agent is in the range of 0.026M to 1M; and
a final molarity of the salt is in the range of 0.15M to 3M; and
adding an injectable RNA-based vaccine having a lipid-based carrier to the solution;
wherein the solution protects against degradation of the injectable RNA-based vaccine having a lipid-based carrier added to the solution in a temperature range of +10 degrees C. to +45 degrees C. for a duration of 3 days to 40 days.

14. The method of claim 13, wherein a final molarity of the buffering agent is in the range of 0.001M to 3M.

15. The method of claim 13, wherein the concentrations of the chelating agent, buffering agent, and salt are characterized by initial molarities, wherein the configurating of concentrations of the chelating agent, buffering agent, and salt comprises diluting the solution to obtain the final molarities for injection.

16. The method of claim 13, wherein a pH of the solution is maintained in a range of 3.5 to 9.

17. The method of claim 16, further comprising adding one or more of hydrochloric acid (HCl), or NaOH to control pH.

* * * * *